US009176117B2

(12) United States Patent
Silver

(10) Patent No.: US 9,176,117 B2
(45) Date of Patent: Nov. 3, 2015

(54) MACROPHAGE HAZARDOUS MATERIAL DETECTION

(75) Inventor: Robert B. Silver, Syracuse, NY (US)

(73) Assignee: Defense Threat Reduction Agency, Dept. of Defense, United States Government, Washington, DC (US)

(*) Notice: Subject to any disclaimer, the term of this patent is extended or adjusted under 35 U.S.C. 154(b) by 293 days.

(21) Appl. No.: 13/523,501

(22) Filed: Jun. 14, 2012

(65) Prior Publication Data
US 2014/0162304 A1 Jun. 12, 2014

Related U.S. Application Data

(60) Provisional application No. 61/496,897, filed on Jun. 14, 2011.

(51) Int. Cl.
C12Q 1/02 (2006.01)
G01N 33/50 (2006.01)
C12N 5/0786 (2010.01)

(52) U.S. Cl.
CPC .......... G01N 33/5055 (2013.01); C12N 5/0645 (2013.01); G01N 33/5014 (2013.01); C12N 2503/02 (2013.01); G01N 2333/4603 (2013.01)

(58) Field of Classification Search
None
See application file for complete search history.

(56) References Cited

U.S. PATENT DOCUMENTS

| 7,737,455 | B2* | 6/2010 | Shum | 257/98 |
| 2003/0064362 | A1 | 4/2003 | Silver | |
| 2003/0207271 | A1* | 11/2003 | Holwitt et al. | 435/6 |
| 2005/0064524 | A1* | 3/2005 | Deutsch et al. | 435/7.23 |

FOREIGN PATENT DOCUMENTS

WO WO-03/027680 A2 4/2003

OTHER PUBLICATIONS

Nianzhen Li et al.; A Calcium-Induced Calcium Influx Factor, Nitric Oxide, Modulates the Refilling of Calcium Stores in Astrocytes; The Journal of Neuroscience, Nov. 12, 2003; 23(32):10302-10310.
Samuel A. Latt et al.; Spectral Studies on 33258 Hoechst and Related Bisbenzimidazole Dyes Useful for Fluorescent Detection of Deoxyonucleic Acid Synthesis; The Journal of Histochemistry and Cytochemistry; vol. 24, No. 1., pp. 24-33, 1976.

(Continued)

Primary Examiner — Robert Mondesi
Assistant Examiner — Thomas J Visone
(74) Attorney, Agent, or Firm — Dinsmore & Shohl LLP; Weston R. Gould

(57) ABSTRACT

Sentinel Cells, respond quickly and differentially to and among various high explosives (e.g., RDX, PETN, HMX, TNT, TNG), taggant (DMDNB), and bacteria, as well as volatiles of commercial C4, Semtex 1A, and military C4. These effects are observable within 5 minutes of exposure, indicate profound biological effects in exposed cells, and are distinctly different from responses to bacteria (e.g., E. coli, mycoplasma, lipopolysaccharide from E. coli, etc.). Quantitative and mechanistic analysis of the observations indicate that the mechanisms that give rise to these responses invoke different subsets of biochemical reactions. The mechanism within the exposed Sentinel Cells is also used in canine olfactory cells (e.g., bomb dogs). The nature of the explosives-induced biological effects provide for a cell based explosives detection system (i.e., a cellular dog nose), as well as a tool for the study of biological effects of energetic materials on humans.

2 Claims, 32 Drawing Sheets

(56) References Cited

OTHER PUBLICATIONS

Committee on the Review of Existing and Potential Standoff Explosives Detection Techniques, National Research Council, "Existing and Potential Standoff Explosives Detection Techniques," 148 pages (2004).

Mostak, Petr, "Vapour and Trace Detection of Explosives for Anti-Terrorism Purposes", Research Institute of Industrial Chemistry, Explosia, Czech Republic, pp. 23-30 (2004).

Leibovitz, A., "The Growth and Maintenance of Tissue-Cell Cultires in Free Gas Exchange with the Atmosphere," Amer. J. Hyg. 78:173-80, 1963 [Sixth US Army Medical Laboratory, Fort Baker, CA].

Silver, Robert B., "Nuclear Envelope Breakdown and Mitosis in Sand Dollar Embryos Is Inhibited by Microinjection of Calcium Buffers in a Calcium-Reversible Fashion, and by Antagonists of Intracelular $Ca^{2+}$ Channels," Developmental Biology, 131, 11-26 (1989).

Strijdom, H. et al., "Direct intracellular nitric oxide detection in isolated adult cardiomyocytes: flow cytometric analysis using the fluorescent probe, diaminofluorescein," Journal of Molecular and Cellular Cardiology, 37 (2004) 897-902.

McConnell, J. Michael, Annual Threat Assessment of the Director of National Intelligence for the Senate Select Committee on Intelligence, Feb. 5, 2008, 47 pages.

Blair, Dennis C., "Annual Threat Assessment of the Intelligence Community for the Senate Select Committee on Intelligence," Feb. 12, 2009, 46 pages.

\* cited by examiner

FIG. 18

MACROPHAGE HAZARDOUS MATERIAL DETECTION

CROSS REFERENCE TO RELATED APPLICATIONS

This application claims priority to U.S. Provisional Application No. 61/496,897, filed Jun. 14, 2012, the entire contents of which are incorporated herein by reference.

GOVERNMENT SPONSORSHIP

Elements of this disclosure were made with government support under grant No. HDTRA1-07-1-0029 awarded by the Defense Threat Reduction Agency. The United States government has certain rights in the invention.

FIELD OF THE INVENTION

The invention relates in general to the detection of organic molecules or ionizing radiation and in particular to a newly isolated stationary macrophage termed a sentinel cell.

BACKGROUND OF THE INVENTION

The United States and its allies are the targets of attacks by terrorists or criminals who use weapons based on energetic materials (EM) such as explosives, biological weapons, or energy weapons. Such attacks may affect personnel and installations with possible significant casualties. In the past decade, the U.S. experienced about 3,000 explosions a year that warranted forensic investigation. (Comm Assessment Sec Tech for Transp, Nat'l Res Coun, 2004; Mostak P (2004); Sanchez et al (2007).

Improved near-range and standoff detection of EM is essential for defeating those who would use EM-based weapons and propellants against the U.S., its allies, and innocent people (McConnell J M (2008) *Annual Threat Assessment of the Director of National Intelligence*; Blair, D C (2009) *Annual Threat Assessment of the Intelligence Community for the Senate Select Committee on Intelligence*.). A spectrum of EM detection tools is necessary to protect and defend people from EM based attacks.

Thus, there exists a need for a robust, selective, and readily tailored detection system for various target species including explosives, chemical and/or biological weapons such as weapons of mass destruction (WMDs) as well as ionizing radiation.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

| Labeling Key for Cytospectrograms | |
|---|---|
| Label | Observed Attribute |
| 1 | NOS Activity |
| 2 | NOS Activity Plateau |
| 3 | NOS Activity Sustained |
| 4 | DNA Labeling - H33342 |
| 5 | Increased Nuclear DNA Signal |
| 6 | Unscheduled DNA Synthesis |
| 7 | Increase in Cell Size |
| 8 | Increased Membrane Surface |
| 9 | Membrane Blebbing |
| 10 | Membrane Peroxidation |
| 11 | Increased Cytoskeleton |
| 12 | Enlarge Nucleus |
| 13 | Lobed Nucleus |
| 14 | Nucleus with Tines |
| 15 | Nuclear Swell-Relax |
| 16 | Cytoplasmic DNA |
| 17 | Arborized Nucleus |
| 18 | Micronuclei Formed |
| 19 | Condensed Chromosomes |
| 20 | Karyomeres |
| 21 | Mirror Image Cells |
| 22 | Nuclear Envelope Breakdown |
| 23 | Mitosis |
| 24 | Emerge from Tissue |
| 25 | "Hunting" Behavior |
| 26 | Apoptosis Induced |

Figure 4A:
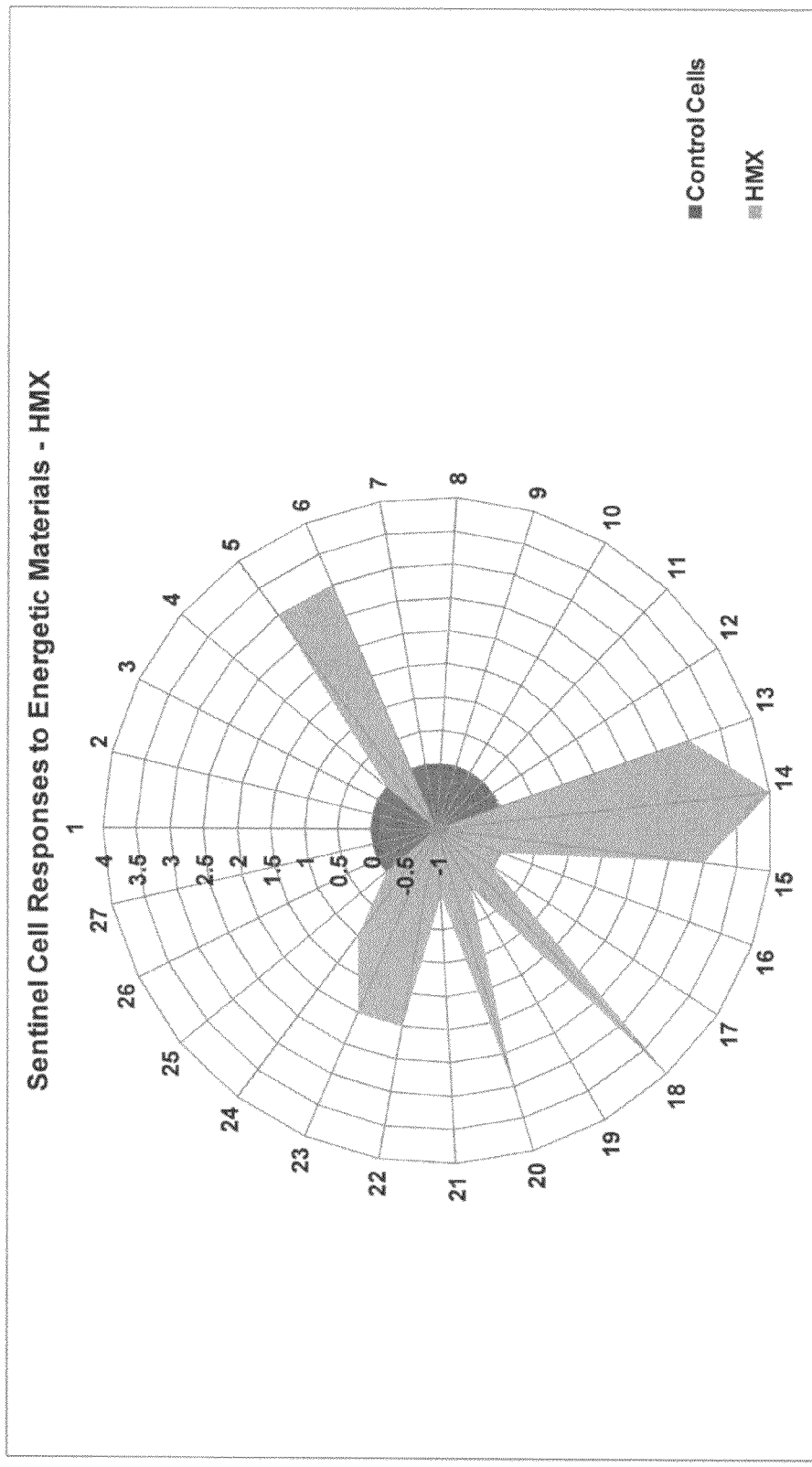
Figure 4B:
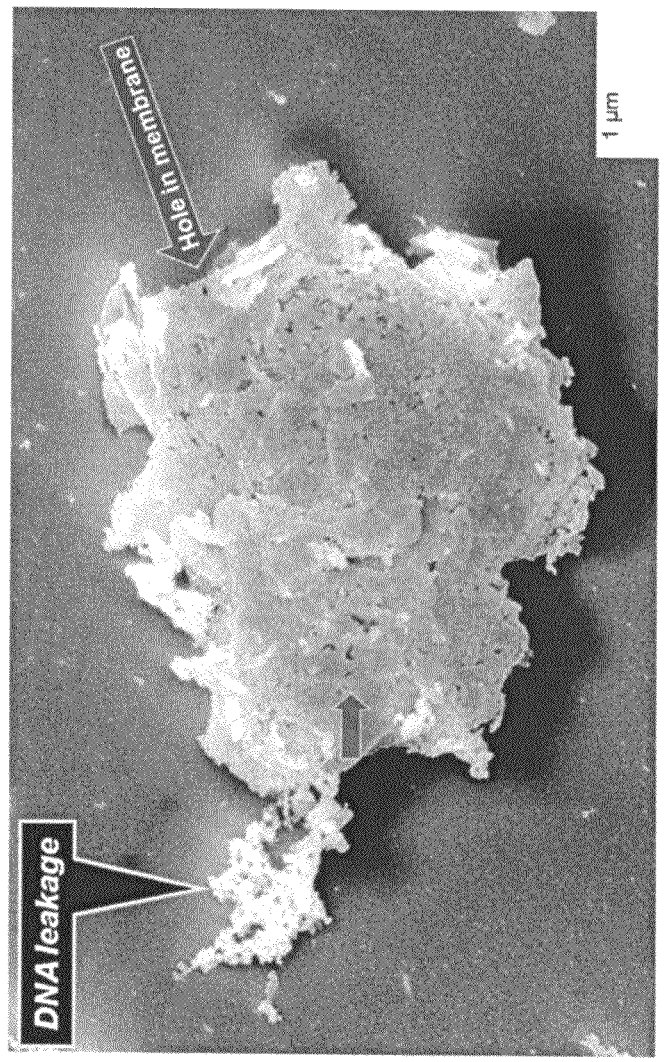
Figure 6A:
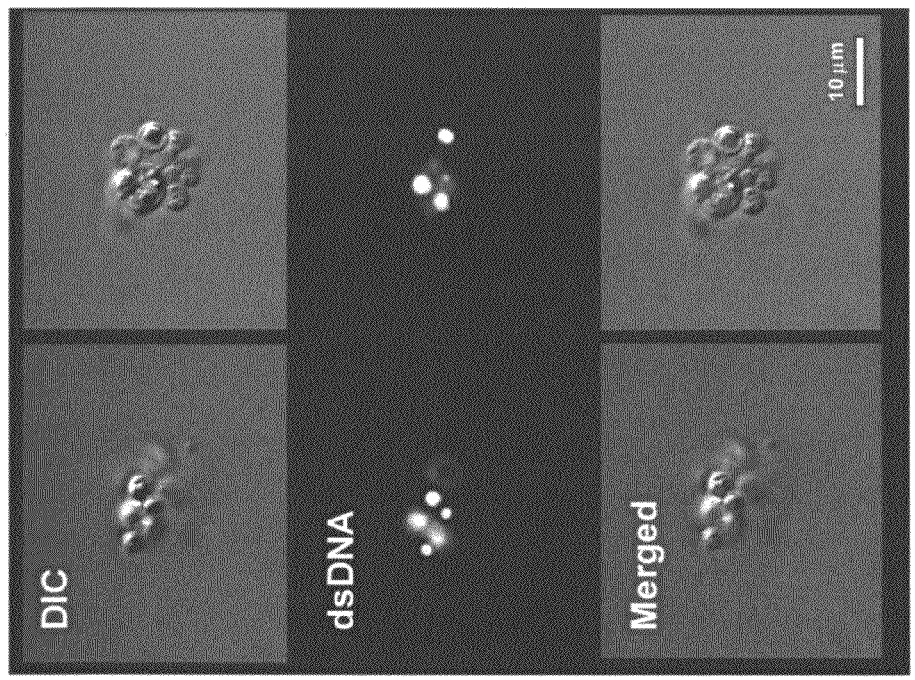
Figure 6B:
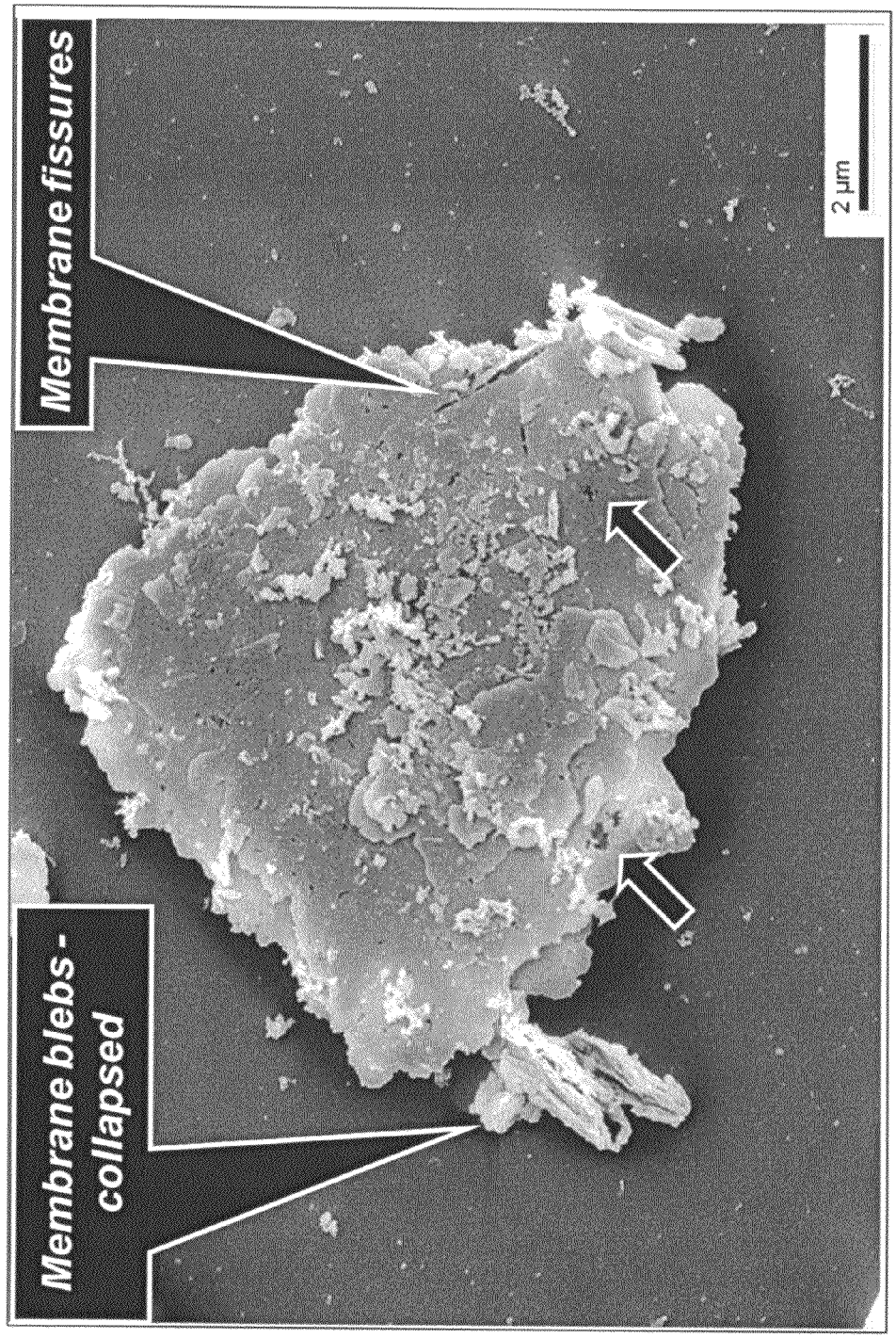
Figure 6C:
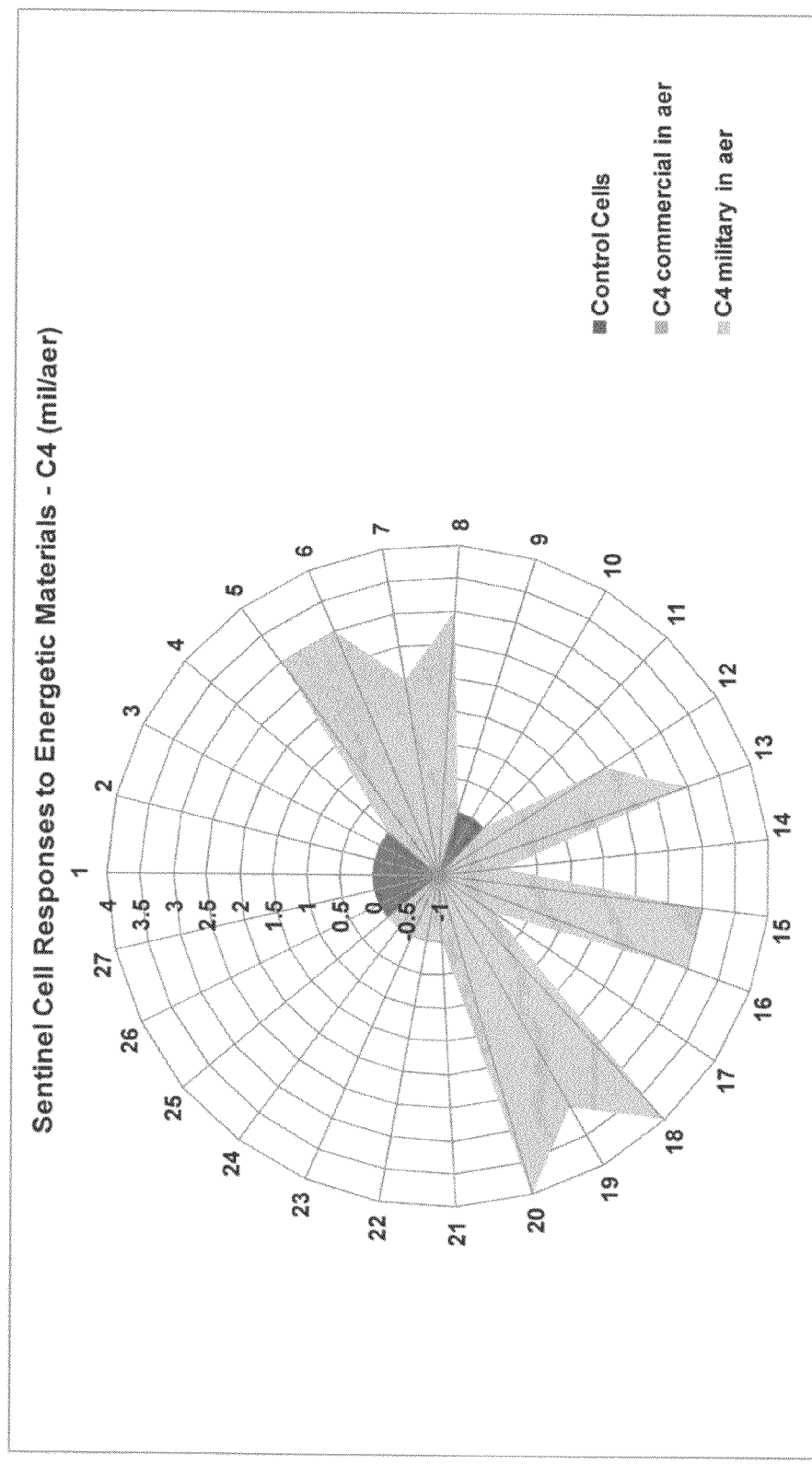
Figure 8:
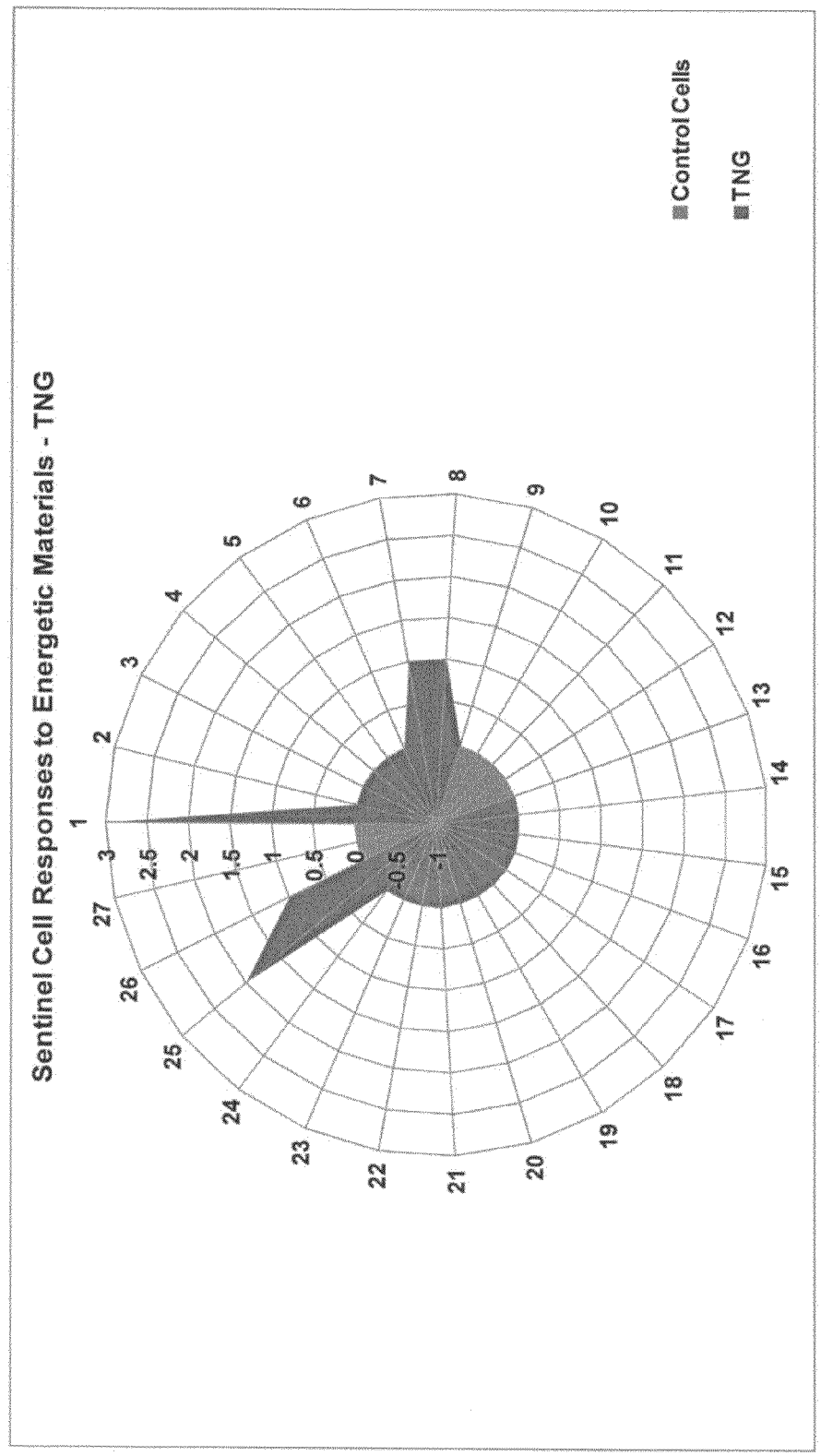
Figure 10:
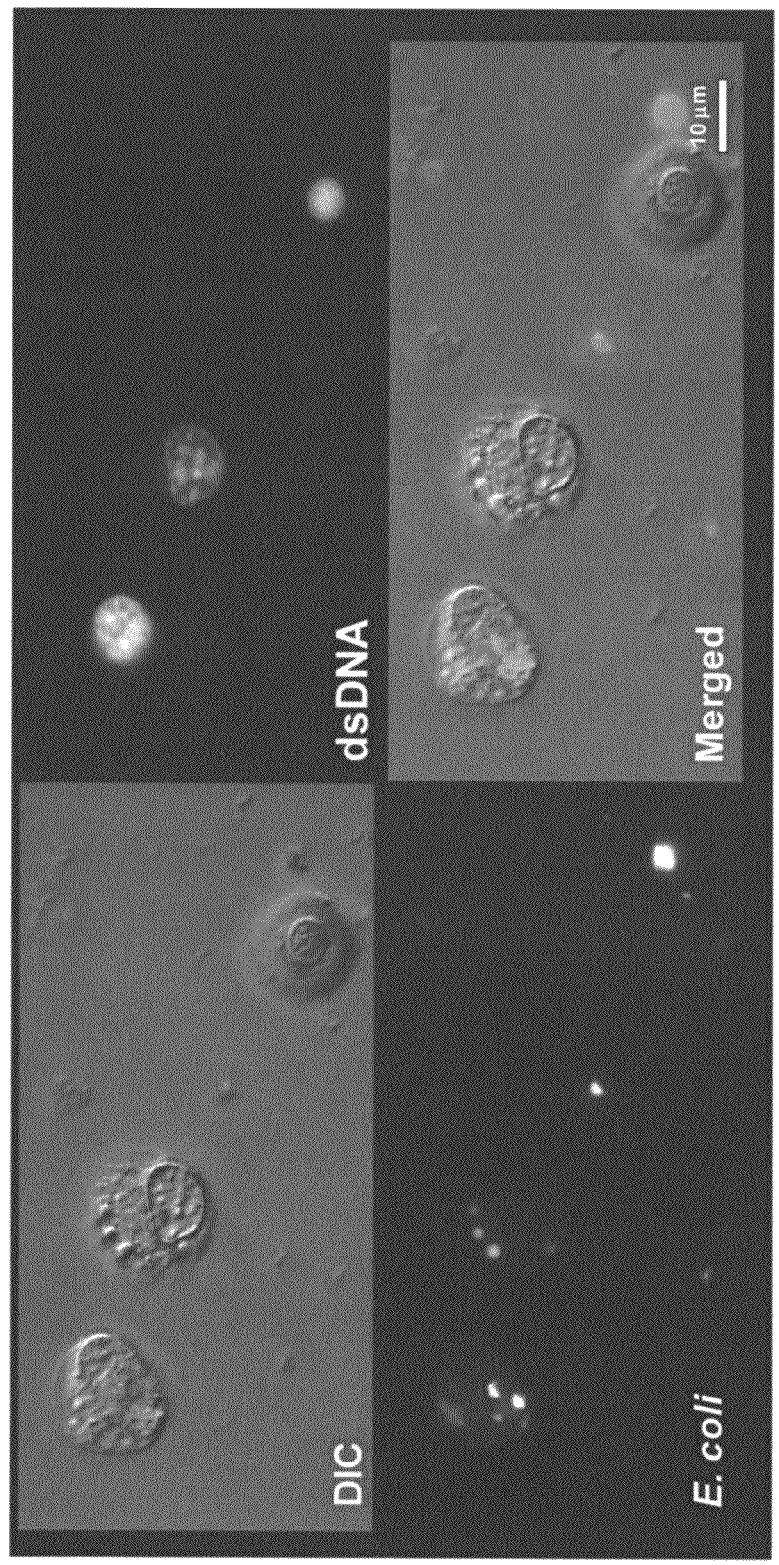
Figure 11:
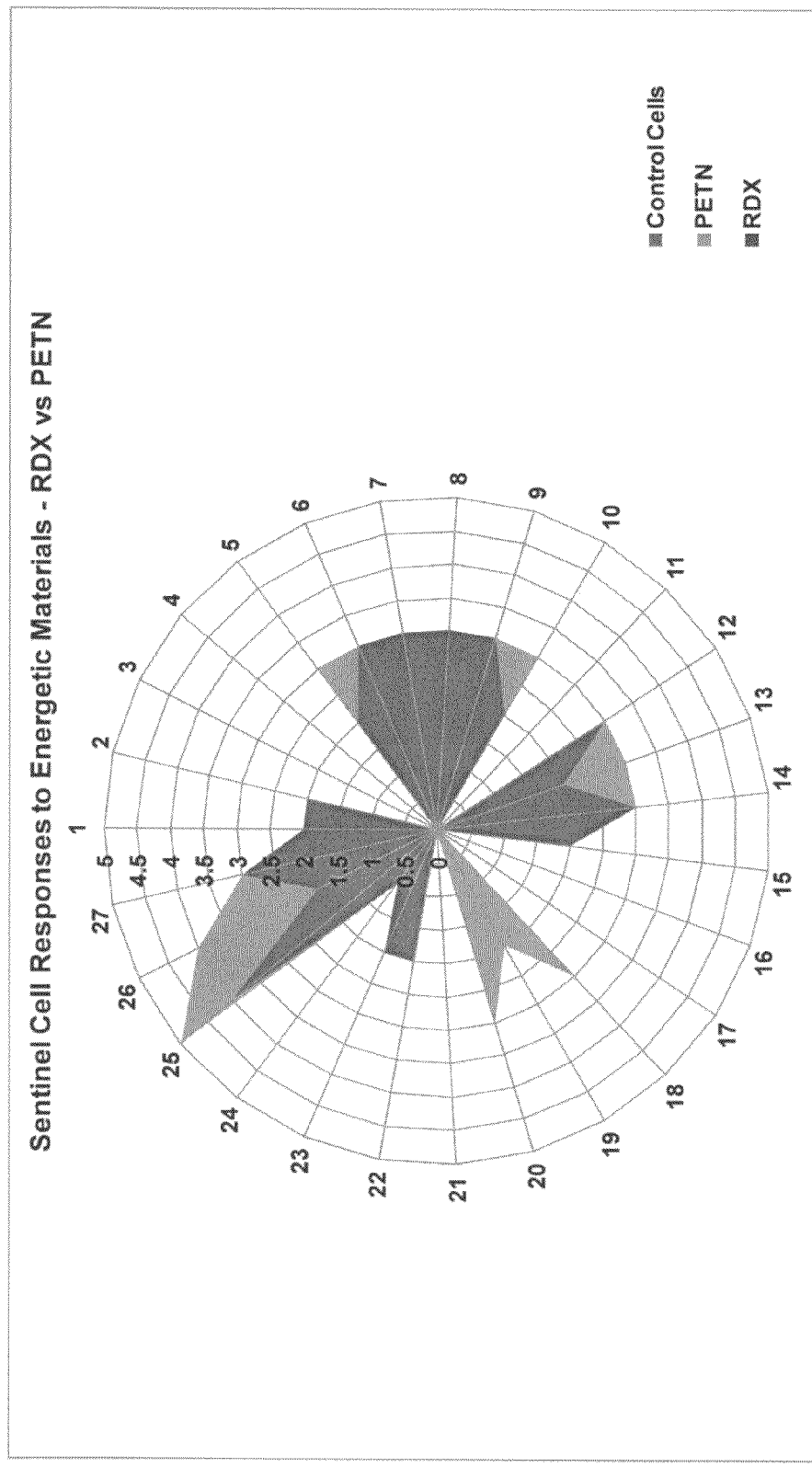
Figure 12:
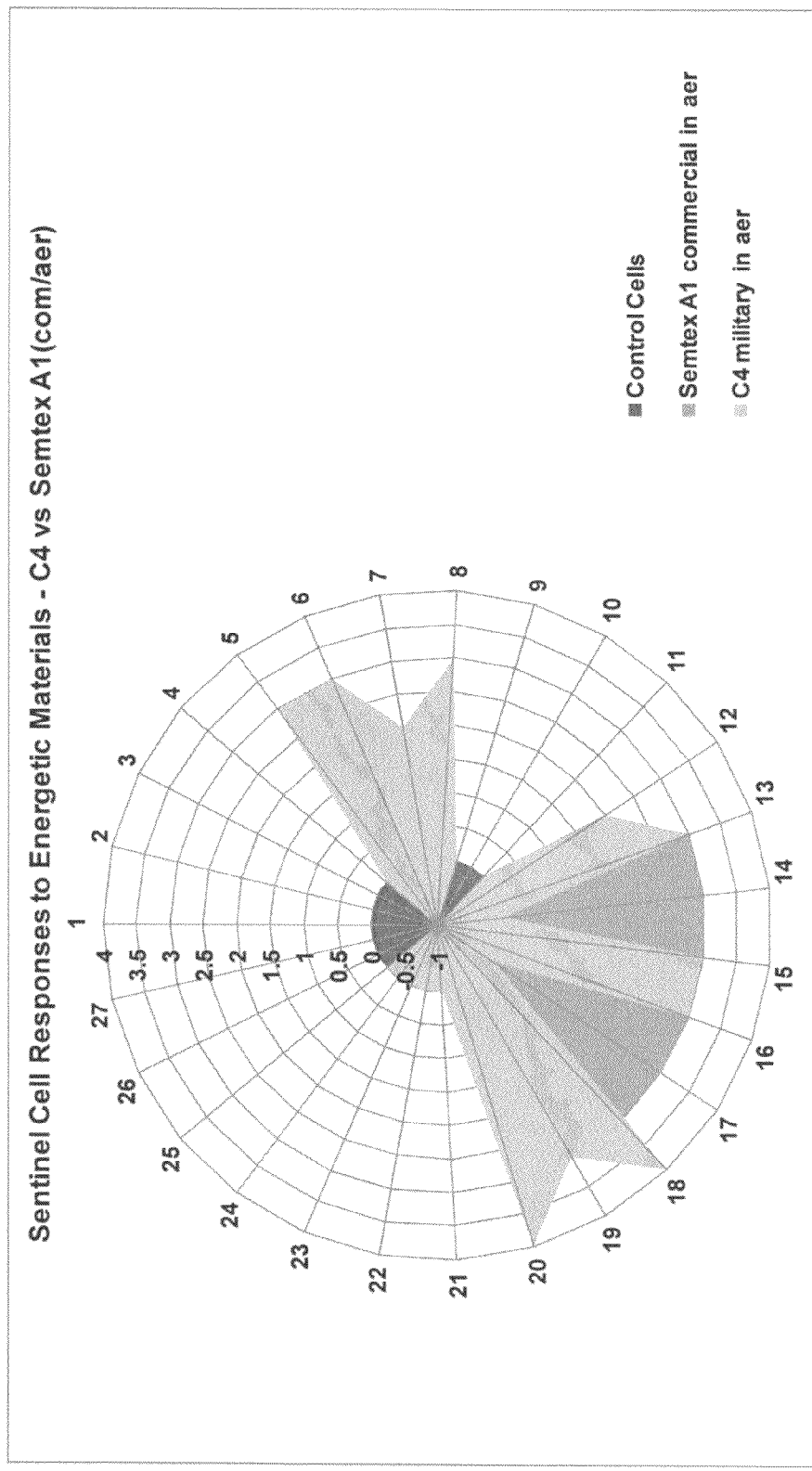
Figure 13:
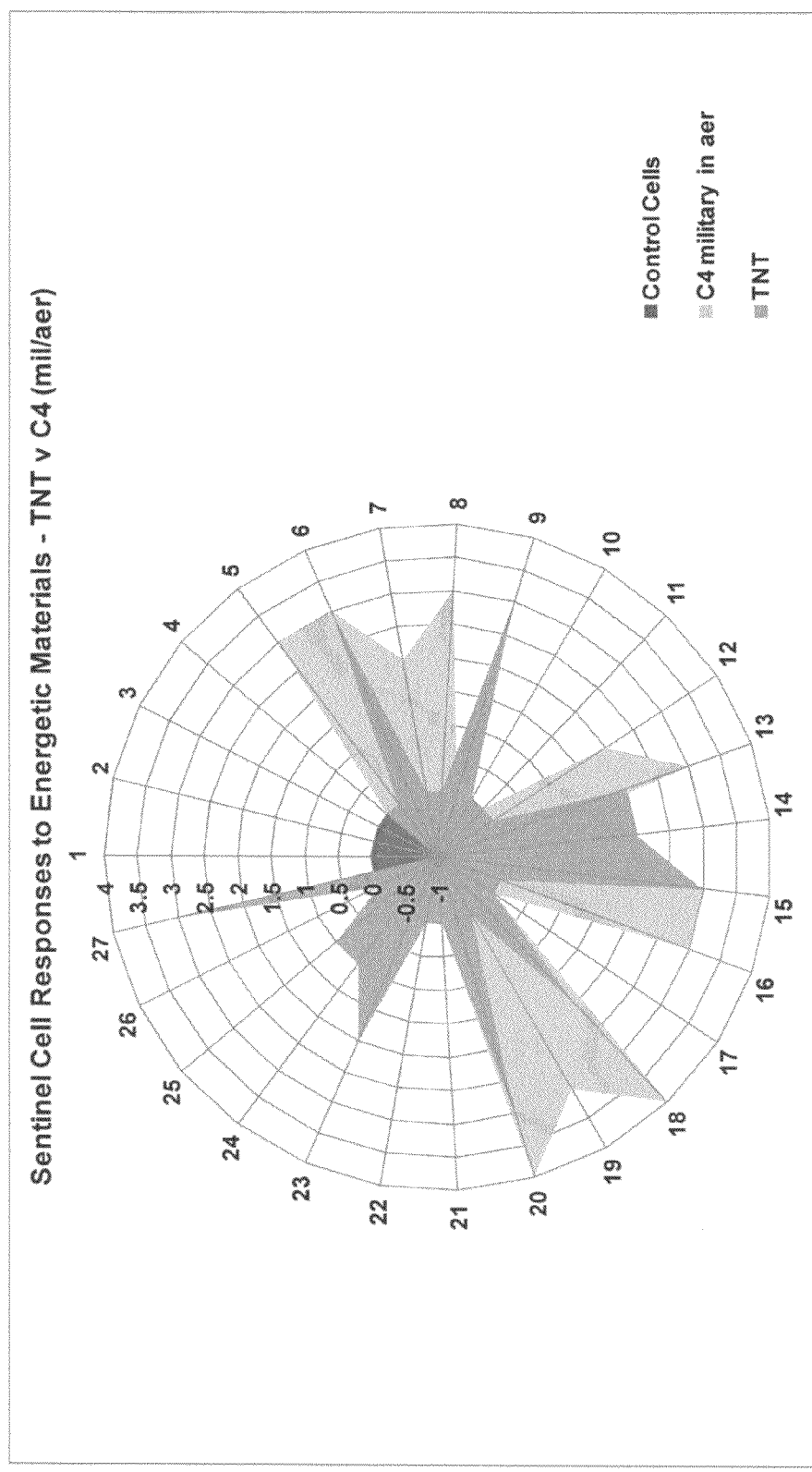
Figure 14:
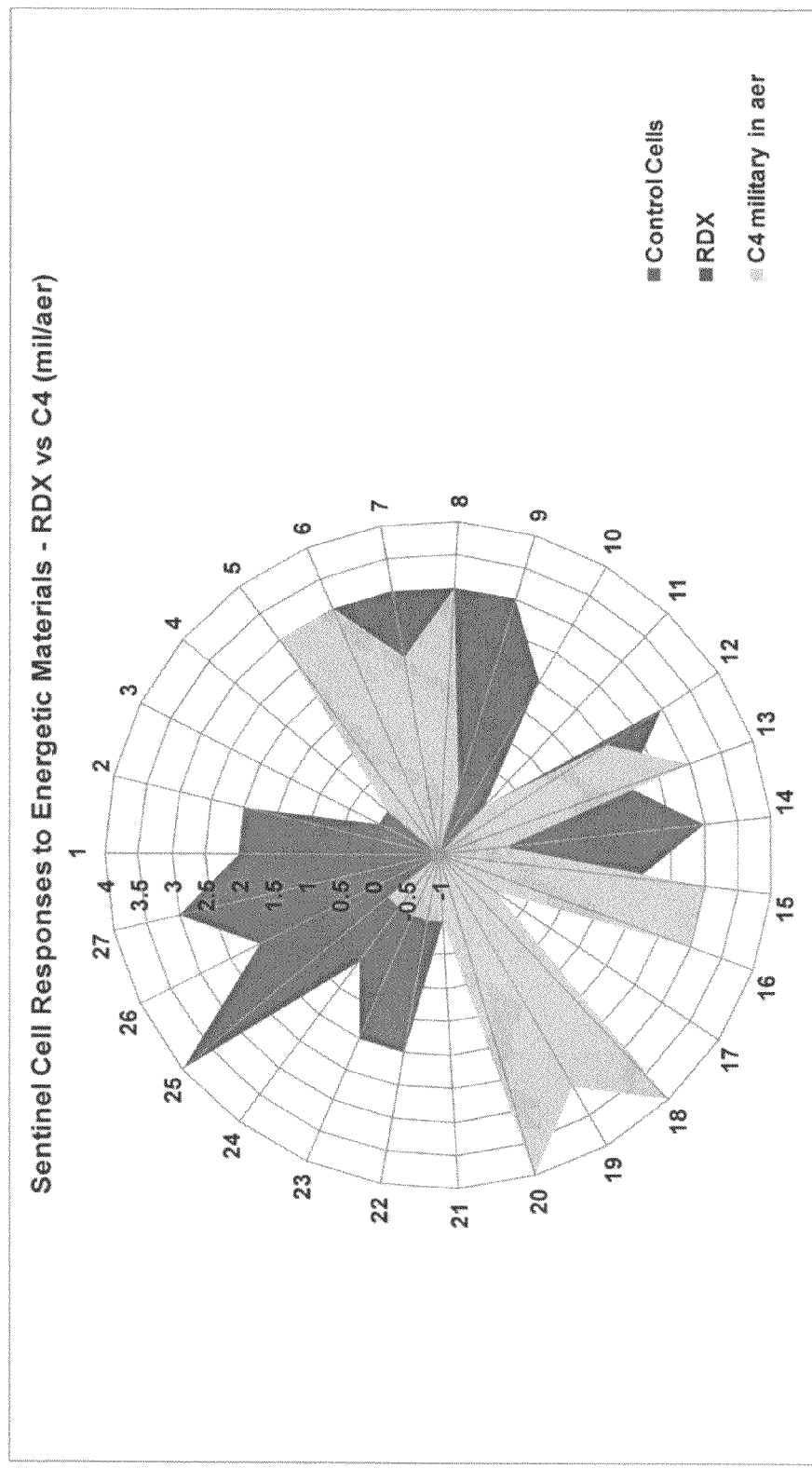
Figure 15:
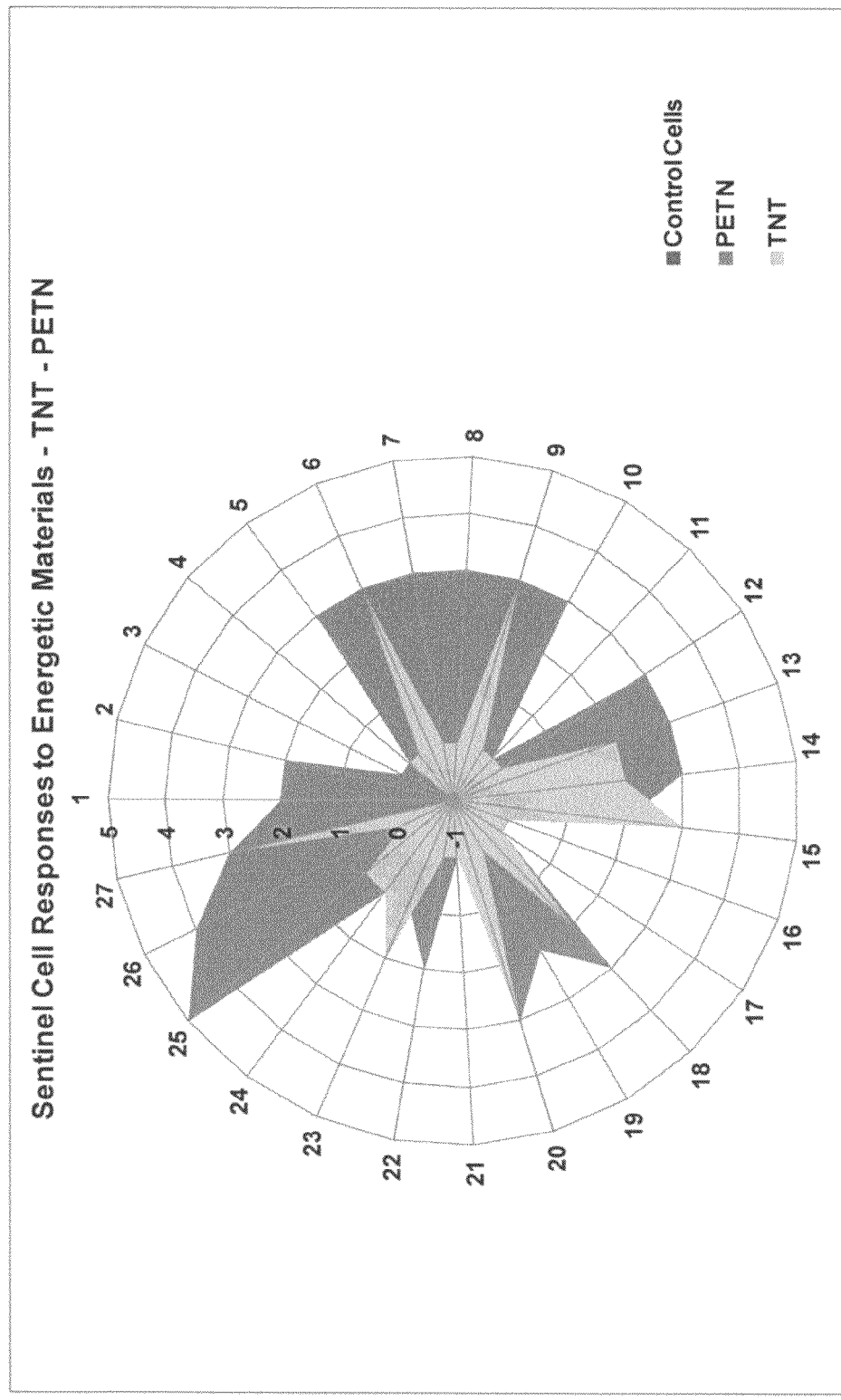
Figure 16:
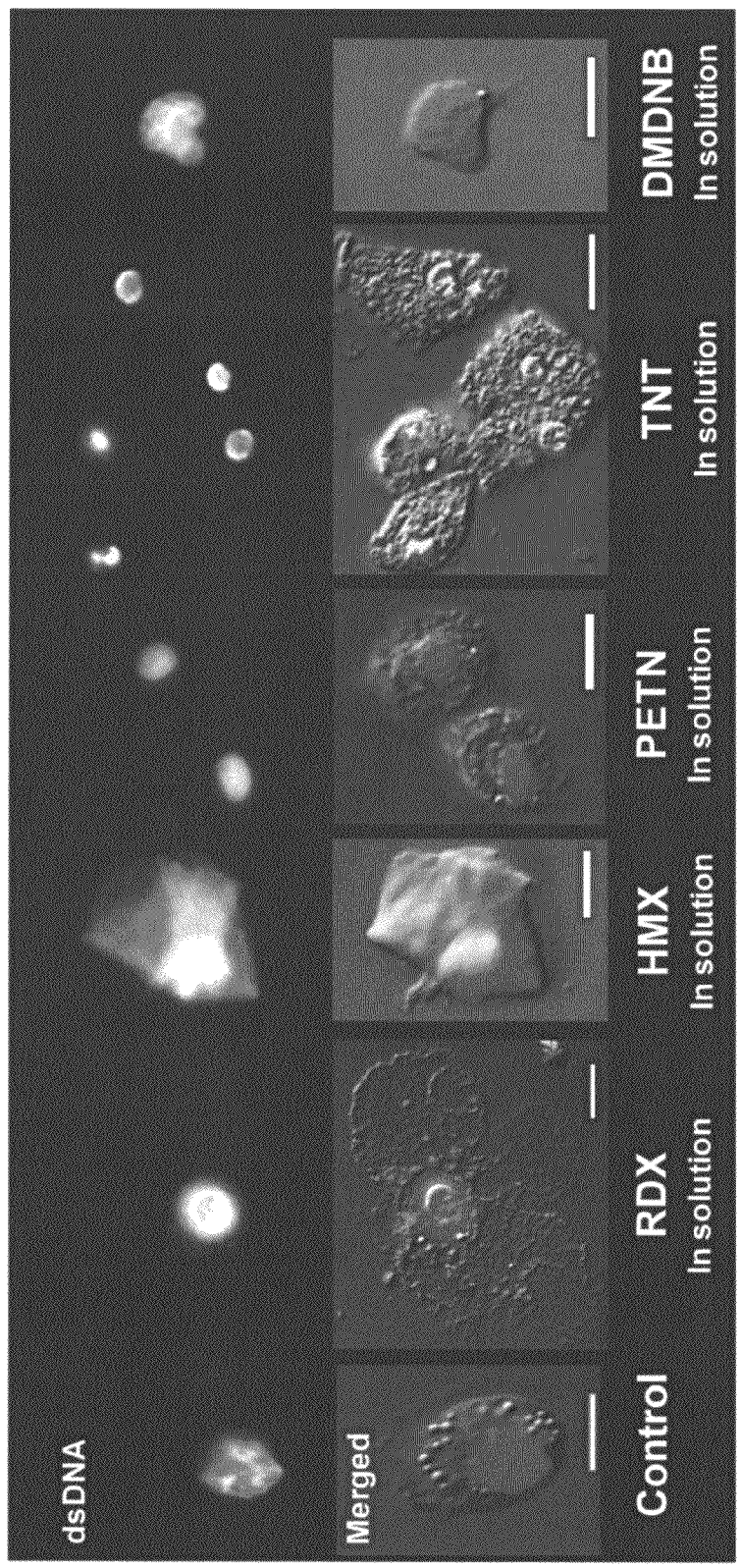
Figure 17:
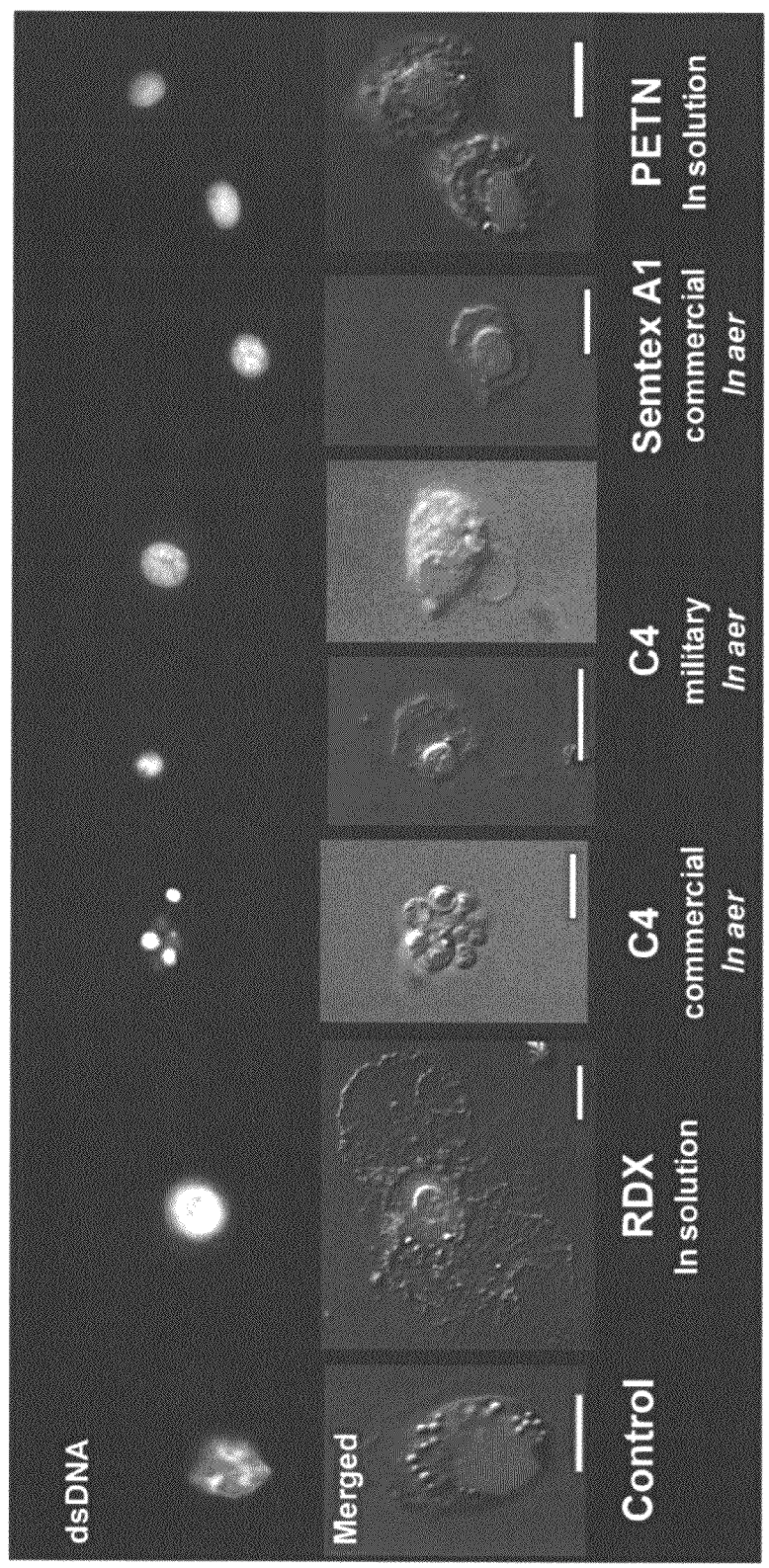
Figure 19:
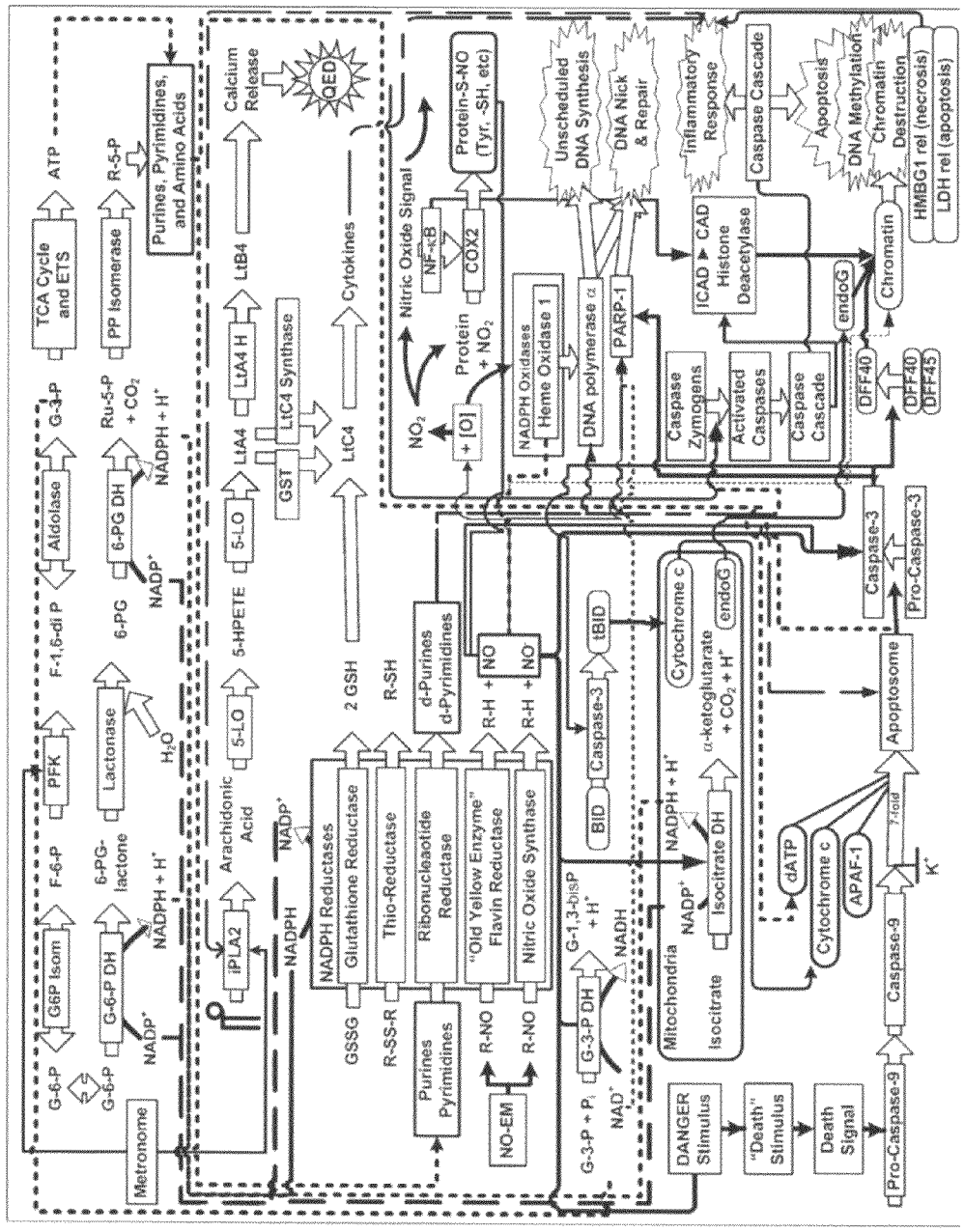

FIG. 3 illustrates sentinel cell responses to PETN depicting (A) NOS and PLA2 activities, (B) cellular morphology, and (C) a graphical display (flower plot) in an EM specific pattern where the responses are as in Table 1;

FIG. 4 illustrates sentinel cell responses to HMX depicting (A) a graphical display (flower plot) in an EM specific pattern where the responses are as in Table 1, and (B) cellular morphology;

FIG. 5 illustrates sentinel cell responses to TNT depicting (A) optical cellular changes; and (B) a graphical display (flower plot) in an EM specific pattern where the responses are as in Table 1;

FIG. 6 illustrates sentinel cell responses to C4 depicting (A) DNA specific responses to EM, (B) optical cellular changes, and (C) a graphical display (flower plot) in an EM specific pattern where the responses are as in Table 1;

FIG. 7 illustrates sentinel cell responses to Semtex A1 depicting (A) and (B) DNA specific responses to EM, and (C) a graphical display (flower plot) in an EM specific pattern where the responses are as in Table 1;

FIG. 8 illustrates sentinel cell responses to TNG depicting a graphical display (flower plot) in an EM specific pattern where the responses are as in Table 1;

FIG. 9 illustrates sentinel cell responses to the taggant DMDNB depicting (A) DNA specific responses to EM, (B) optical cellular changes, and (C) a graphical display (flower plot) in an EM specific pattern where the responses are as in Table 1;

FIG. 10 illustrates sentinel cell responses to the *E. coli* K12 depicting DNA specific responses to EM using sentinel cells where the responses are as in Table 1;

FIG. 11 illustrates an overall comparison of cellular responses depicted as a flower plot of the relative extent of each response between PETN and RDX illustrating the ready ability to distinguish these two EM using sentinel cells where the responses are as in Table 1;

FIG. 12 illustrates an overall comparison of cellular responses depicted as a flower plot of the relative extent of each response between Semtex A1 (commercial (com)) and C4 (aerosol (aer)) illustrating the ready ability to distinguish these two EM using sentinel cells where the responses are as in Table 1;

FIG. 13 illustrates an overall comparison of cellular responses depicted as a flower plot of the relative extent of each response between TNT and C4 (military (mil), aerosol (aer)) illustrating the ready ability to distinguish these two EM using sentinel cells where the responses are as in Table 1;

FIG. 14 illustrates an overall comparison of cellular responses depicted as a flower plot of the relative extent of each response between RDX and C4 (military (mil), aerosol (aer)) illustrating the ready ability to distinguish these two EM using sentinel cells where the responses are as in Table 1;

FIG. 15 illustrates an overall comparison of cellular responses depicted as a flower plot of the relative extent of each response between TNT and PETN illustrating the ready ability to distinguish these two EM using sentinel cells where the responses are as in Table 1;

FIG. 16 illustrates various cellular changes in sentinel cells following exposure to various EM;

FIG. 17 illustrates various cellular changes in sentinel cells following exposure to various EM;

Figure 18:
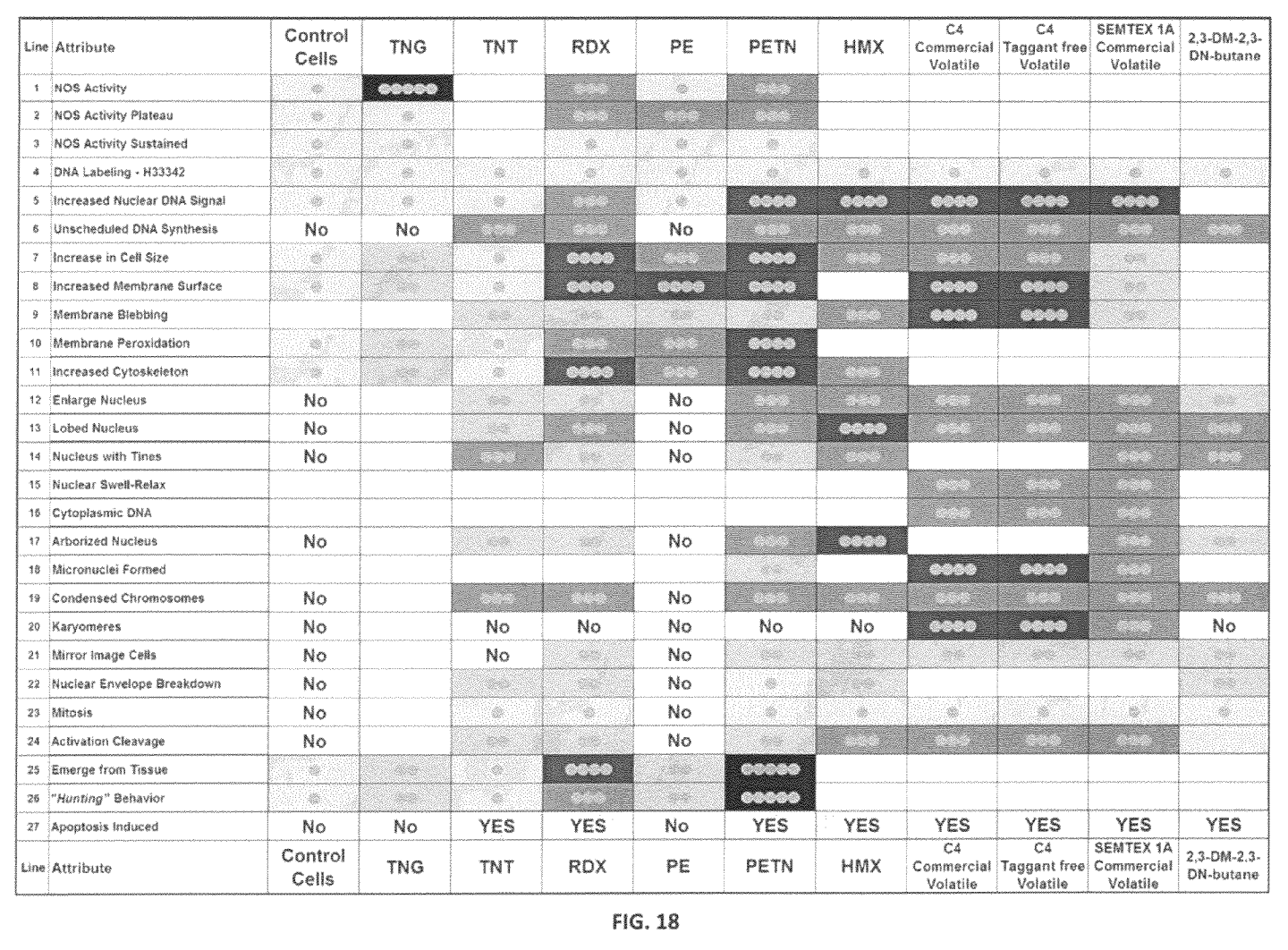

FIG. 18 illustrates a summary and relative extent of various cellular responses to numerous energetic materials;

FIG. 19 is a depiction of cellular responses in sentinel cells upon exposure to one or more EM.

DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes, kits, or compositions are described as an order of individual steps or using specific materials, it is appreciated that described steps or materials may be interchangeable such that the description of the invention includes multiple parts or steps arranged in many ways as is readily appreciated by one of skill in the art.

Compositions and processes are provided for detection of one or more energetic materials (EM) including explosives, chemical and/or biological weapons, as well as ionizing radiation using one or more sentinel cells. Sentinel Cells (SC) are a stationary macrophage that is newly identified in, isolated, and optionally cultured from a poikilothermic teleost. This specialized stationary macrophage improves prior detection methods and is amenable to integration onto existing technologies thereby extending their capabilities.

The SCs are a cell-based detector for EM with rapid response to exposure to a target species. These cells possess unexpectedly long life in culture (35+ months without exchange of media) as well as low metabolic and culturing requirements. These are factors distinguishable from other cell-based, laboratory instrument-based or colorimetric/chemical methods.

An isolated, culture stable, and uniquely responsive set of stationary macrophages are provided termed Sentinel Cells (SC). SC are isolated stationary macrophages that possess great culture stability and responsiveness to energetic materials, as well as other agents. Stationary macrophages are illustratively isolated from warm-blooded animals or cold-blooded animals. Illustrative stationary macrophage sources include birds, primates, bovines, equines, or murines, echinoderms (e.g., sea urchins, star fish, sand dollars, among others), teleost fishes, elasmobranchs (e.g., skates, rays), mollusks (e.g., squid, cuttlefish, among others), amphibians, or other animals. In some embodiments, a SC is isolated from the vestibular labyrinths (or remain as a portion of an isolated vestibular labyrinth) of a migratory poikilothermic teleost—the Oyster Toadfish (*Opsanus* sp.). Isolated SC show excellent responsiveness when allowed to passively migrate from opened labyrinths to a culture surface (substrate) such as a prepared glass cover slip, however, it is appreciated that SC can be isolated by collagenase digestion of the surrounding tissue followed by a recovery period for the isolated cells. SC remain viable and biologically active under culture conditions of ambient temperature (−3° C. to 30° C.) in the absence of serum, antibiotics, antifungals, or required supplemental $CO_2$.

Illustrative media for the culture of SC include any media suitable for culturing cells in the absence of supplemented $CO_2$. An illustrative media is Liebovitz L-15 media, optionally supplemented with L-glutamine commercially available from Sigma-Aldrich, St. Louis, Mo. Leibovitz: A, *Am. J. Hyg.*, 1963; 78:173-180.

The isolated stationary macrophages, SC, are cultured on a substrate. A substrate is any surface to which an SC can adhere, or contact for maintenance of responsiveness. Illustrative examples of a substrate include: glass; plastics such as polystyrene, hydrophilic polytetrafluoroethylene (PTFE), polycarbonate, polyethylene terephthalate; among others; or modifications thereof, illustratively modified with poly-L-lysine, collagen or other protein, MATRIGEL, or other modification known in the art. Optionally, a substrate is a membrane that alone or in combination with a solid surface serves as a culture location of SC. In some embodiments, a substrate is glass. Optionally a glass substrate is a glass cover-slip such as those typically used for microscopy applications. In some embodiments, a substrate is subjected to a pre-treatment process (biocleaned) to ensure clean and toxin free substrate surface for the isolation of SC.

SC respond rapidly in complex, characteristic and differentiable manner to energetic materials (EM) such as explosives (e.g., RDX, PETN, HMX, TNT, TNG), taggants (e.g., 2,3-dimethyl-2,3-dinitro-butane (DMDNB), bacteria, and toxins such as biological toxins illustratively lipopolysaccharide (LPS), *Staph* enterotoxins, or biological weapons, among others. SC respond differently to different EM such that a response profile is detectable that indicates the presence or the absence of EM in contact with or proximity to SC. These effects are observable within 5 minutes of initial exposure, often within 1 minute following initial exposure, and indicate profound biological effects in exposed cells, and are distinctly different from responses to bacteria (e.g., *E. coli*, mycoplasma, lipopolysaccharide from *E. coli*, etc.).

Cells that qualify as SC are capable of surviving and remaining biologically active in culture for more than 25,000 hours (more than 1,040 days) at −3° C. to 30° C., i.e., exceeding a target for on-site sensor deployment target of 1,600 hours, and remain responsive to EM. Thus, SC can perform as cellular "dog noses" for the highly sensitive detection of EM contacting or in proximity to the SC. SC respond to EM in solution at concentrations in the range of ppb and ppt (e.g. RDX, PETN, HMX, etc.). Other concentrations are operable as well.

Illustrative cellular responses of SC include increased activity of nitric oxide synthase (NOS), nitric oxide (NO) levels, plateau of NO activity, sustainment of NO activity, increases or decreases in double stranded DNA, increases in nuclear DNA levels, unscheduled DNA synthesis, increase in cell size (diameter on surface), increased membrane surface, membrane blebbing, membrane peroxidation, increased cytoskeleton, enlarged nucleus, lobed nucleus, nucleus with tines, nuclear swell-relax, cytoplasmic DNA, aborization of the nucleus, formation of micronuclei, chromosome condensation, karyomeres, mirror image cells, breakdown of the nuclear envelope, onset of mitosis, emergence from tissue, hunting behavior, induction of apoptosis, or any combination thereof. Different EM produce different levels of each of the above responses in SC such that the type and level of each response represents a distinctive output that is specific to the EM type allowing determination of the EM that was caused the response.

SC have numerous advantages in that SC do not get tired or distracted as can bomb dogs, and do not suffer from distractions. Without being limited by one particular theory, it is believed that the mechanism within exposed SC is similar to that used in odor detection by canine olfactory cells (e.g., bomb dogs). The nature of the EM-induced biological effects indicate the SC operate as an EM detection system (i.e., a cellular dog nose), as well as for study of the biological effects of EM (e.g., undetonated explosives) on humans.

Sentinel Cells, respond quickly and differentially to and among various EM illustratively including high explosives (e.g., RDX, PETN, HMX, TNT, and TNG), taggant (DM-DNB), and bacteria, as well as volatiles of commercial C4 and Semtex1A and military C4, among other EM. These effects are observable within 5 minutes of exposure, indicate profound biological effects in exposed cells, and are distinctly different from responses to bacteria (e.g., E. coli, mycoplasma, lipopolysaccharide from E. coli, etc.). Quantitative and mechanistic analyses of SC responses indicate that the mechanisms that give rise to these responses invoke different subsets of biochemical reactions.

Sentinel Cell responses are: synergistic, and reproducible; suggest alterations in substrate and co-factor levels and possible inhibitory role; and differ for different energetic materials and for bacteria. These responses are not simply due to: molecular shape of EM (incl. aromatic or aliphatic properties); number of nitrate groups present in EM; cell surface or cytosolic receptors specific for any particular EM; or other "first-order" factors.

Also provided are methods for detection of EM either in solution, solid media, volatiles from EM, or aerosols of EM. A method includes exposing a SC to an EM and optionally detecting a response of the SC that is characteristic of the EM to which the SC is exposed.

As used herein, energetic materials (EM) are any material (chemical, biological, environmental) or energy that will cause a SC to produce a response. Illustrative examples of EM include: 1,3,5-trinitro-1,3,5-triazacyclohexane (1,3,5-trinitroperhydro-1,3,5-triazine; RDX); 1,3,5,7-tetranitro-1,3,5,7-tetrazocane (1,3,5,7-tetranitro-1,3,5,7-tetrazocane; HMX); 2,2-bis(hydroxymethyl)1,3-propanediol (pentaerythritol tetranitrate; PETN); 2,4,6-trinitrotoluene (2-methyl-1,3,5-trinitrobenzene; TNT), 1,2,3-trinitroxypropane (trinitroglycerin; TNG); 2,3-dimethyl-2,3,-dinitrobutane (2,3-dimethyl-2,3-dinitrobutane; DMDNB); triacetone triperoxide (TATP); hexamethylene triperoxide diamine (HMTD); other peroxide or nitrate based explosive materials; gunpowder(s); pentaerythritol (2,2-Bis(hydroxymethyl)1,3-propanediol; PE); bacteria such as mycoplasma and E. coli; biological toxins such as endotoxins illustratively, lipopolysaccharide (LPS); military or commercial grades of C4; Semtex A1; Semtex H; pesticides, illustratively, diazinon, parathion, phorate, fenchlorphus, and chlorpyrifos; nerve agents, illustratively VX (O-ethyl S-[2-(diisopropylamino)ethyl]methylphosphonothioate), GA (ethyl N,N-dimethylphosphoramidocyanidate), GB (propan-2-yl methylphosphonofluoridate), and GD (3,3-Dimethylbutan-2-yl methylphosphonofluoridate); a taggant such as 2,3-dimethyl-2,3-dinitro-butane (DMDNB); other chemical threat agents; other biological threat agents; other radiological threat agents; among others; and combinations thereof.

EM are optionally present in solution from 0.01 nM to 1 µM or any value or range therebetween, optionally 0.5 to 100 nM, or any value or range therebetween. It is appreciated that greater concentrations are operable. In some embodiments, EM are volatiles or aerosols from a source EM material.

As used herein the term "exposing" is placing an EM source in sufficient proximity to a SC such that contact between an EM or a component thereof, occurs with the SC. In some embodiments, exposing is directly contacting a solution of EM with an SC. Optionally, exposing is placing a material that is or produces EM volatiles in sufficient proximity to a SC that the volatile contacts the SC. Optionally, contact is placing the SC within range of radiation that acts as an EM such that the radiation contacts the SC.

SC are exposed to EM for an exposure time. The exposure time is anywhere from 1 second to 30 minutes or more. An exposure time is optionally 1, 2, 3, 4, 5, 6, 7, 8, 9, 10, 15, 20, 30, 40, 50 seconds or more. Optionally, an exposure time is 1, 2, 3, 4, 5, 6, 7, 8, 9, 10, 15, 20, 30, 60 minutes or more. Optionally, an exposure time is 1, 2, 3, 4, 5, 6, 7, 8, 9, 10, 20, 30, or more days.

A response is detected in a SC during and optionally following exposure to EM. A response is any detectable response in a cell such as: changes in morphology; DNA type, level or expression; protein activity or level; changes in membrane morphology; among others, or combinations thereof. Illustrative examples of a response include NOS activity, plateau of NO levels, sustainment of NO levels, increases or decreases in double stranded DNA, increases in nuclear DNA levels, unscheduled DNA synthesis, increase in cell size (diameter on surface), increased membrane surface, membrane blebbing, membrane peroxidation, increased cytoskeleton, enlarged nucleus, lobed nucleus, nucleus with tines, nuclear swell-relax, cytoplasmic DNA, aborization of the nucleus, formation of micronuclei, chromosome condensation, karyomeres, mirror image cells, breakdown of the nuclear envelope, onset of mitosis, emergence from tissue, hunting behavior, induction of apoptosis, or combinations thereof.

Figure 1:
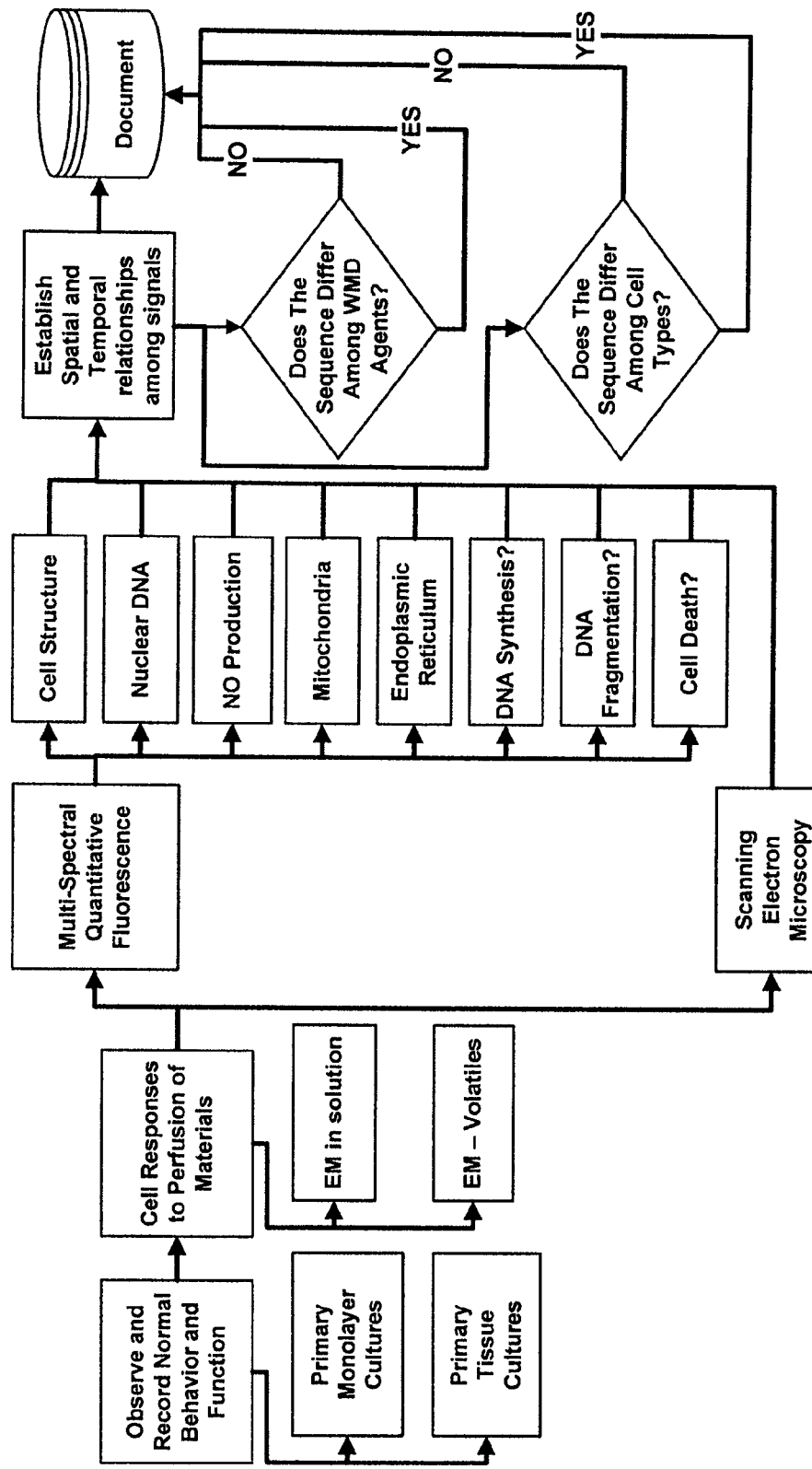
FIG. 1 is a flow chart illustrating an overall process of exposing a sentinel cell to an energetic material and detecting alterations in the cells using techniques such as microscopy as well as establishing relationships among the signals.

In some embodiments, detecting the presence or absence of EM is optionally performed by a process as broadly illustrated in FIG. 1A. Cells in culture as single layer adherent cells to a substrate are labeled using standard known techniques so that cellular organization and EM responses are detectable. The labeled cells are subjected to light microscopy during exposure to EM for the detection and recording of SC responses to the EM. The data are recorded and analyzed for quantitation or relative response levels. The magnitude of each analyzed response provides a response spectrum that is indicative of the particular EM exposed to the cells.

Detecting a response is optionally performed at one or more individual time points, or for a response time. A response time is optionally from 1 second to 30 minutes or more, or any value or range of time therebetween. Optionally, an exposure time is equal to or less than a response time. As such, a response time is optionally the same as an exposure time. A response time is optionally, 1, 2, 3, 4, 5, 6, 7, 8, 9, 10, 15, 20, 30, 40, 50 seconds or more. Optionally, a response time is 1, 2, 3, 4, 5, 6, 7, 8, 9, 10, 15, 20, 30, 60 minutes or more. Optionally, a response time is 1, 2, 3, 4, 5, 6, 7, 8, 9, 10, 20, 30, or more days.

NO levels, the rate of NO production, plateau NO levels, and sustained NO activity are illustratively measured and optionally quantified by methods known in the art. Illustratively, SC are incubated with a fluorophore or other detection agent whereby increases in NO levels or activity are detectable by alteration in levels of fluorescence. Nitric oxide synthase levels are optionally detectable by incubating cells with the NO fluorophore 4-amino-5-methylamino-2',7'-difluorofluorescein diacetate (DAF-FM diacetate; D-23844; $\lambda_{Ex}$: 495 nm; $\lambda_{Em}$: 515 nm; Molecular Probes/Invitrogen, Carlsbad, Calif.). DAF-FM-diacetate enters cells by facilitated diffusion, whereupon cytosolic esterases remove the acetate moieties leaving DAF-FM soluble and trapped in the aqueous cytosol. Nitric oxide produced in the labeled cytosol is then trapped by the DAF-FM which produces a fluorescent triazole at intracellular pHs that is about 160-fold more intense than the un-reacted DAF-FM diamine, and which is readily monitored with a light microscope. Illustrative methods of detecting and optionally quantifying NO by fluorescent labeling and light microscopy in real time are illustratively found in Li, N, et al., *J. Neurosci*, 2003; 23:10302-10310. These labeling and detecting methods are suitable for detecting NO levels such as NOS activity, plateau of NO levels, sustainment of NO levels simply by detecting NO levels over a response time.

Methods of staining SC cell DNA for visualization, localization, and measurement of DNA and associated compartments are illustratively performed by methods known in the art. Illustratively, one or more DNA specific fluorophores are used to monitor changes in DNA levels, morphology, level of double strandedness, and location. Visualization of DNA can also be used to detect and measure nuclear envelope breakdown, nucleus size, nucleus structure and shape, presence or absence of micronuclei, presence or absence of karyomeres, and mitosis, among others, and combinations thereof. In some embodiments, real-time microscopy is used to detect increases or decreases in double stranded DNA, increases in nuclear DNA levels, unscheduled DNA synthesis, enlarged nucleus, lobed nucleus, nucleus with tines, nuclear swell-relax, cytoplasmic DNA, aborization of the nucleus, formation of micronuclei, chromosome condensation, karyomeres, mirror image cells, breakdown of the nuclear envelope, onset of mitosis, among others. Optionally, chromosomal DNA is labeled with the DNA-specific bisbenzamide dye Hoechst H33342 (H21492; Molecular Probes, Carlsbad, Calif.). Double stranded DNA is optionally detected and optionally localized by labeling with fluorescent DNA-selective dyes such as Hoechst 33342 (H33342), Hoechst 33358 (H33358), 4',6-diamidino-2-phenylindole, dihydrochloride (DAPI), among others, or combinations thereof. The localization of DNA is optionally monitored in real-time by microscopy. Illustratively, the localization of DNA to the nucleus is interrupted by exposure of SC to an EM such as HMX, which is detectable by cytoplasmic localization of dsDNA to the cytoplasmic space. Illustrative methods of detecting DNA synthesis, localization of DNA, etc. are illustratively found in Latt and Stetton, *J. Histochem. Cytochem.*, 1976; 24:24-33; and Silver R, *Dev. Biol.*, 1989; 313:11-26.

In some embodiments phospholipase $A_2$ (PLA2) activity levels are used as a response to detect the presence or absence of EM. PLA2 activity is optionally measured by the rate or extent of cleavage of a synthetic substrate for PLA2. Optionally, a PLA2 substrate is N-((6-(2,4-dinitrophenyl)amino) hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6). PLA2 activity results in cleavage of the BODIPY-labeled sn2-chain of the PED6 molecule, which separates the BODIPY from the remainder of the PED6 molecule, and thus removes the intramolecular quenching of the BODIPY resulting in a bright green emission. Illustrative methods for the detection of PLA2 activity are found in Hendrickson, H. S., et al., Anal Biochem., 1999; 276:27-35.

The detection of mitochondrial responses is optionally achieved by the specific labeling of mitochondria using MitoTracker Deep Red (M22426, Molecular Probes, Invitrogen, Inc.) and microscopy.

Membrane characteristics such as the labeling of the endoplasmic reticulum (ER) are illustratively performed by specific labeling of the ER. Illustrative reagents for labeling the ER include a fluorophore conjugated to glibenclamide, which binds to sulphonylurea receptors predominant on the ER. Such detection reagents are illustratively available from Invitrogen, Corp., Carlsbad, Calif. Protocols for staining live cells are available from the manufacturer.

In some embodiments, a combination of labels is used to detect responses in EM. The fluorescent characteristics or other labeling characteristics of the labels are optionally distinguishable by detection methods such that one label does not interfere with another label, or the localization and output of optically overlapping labels allows their simultaneous use. Optionally, the labels listed in Table 2 are used simultaneously.

TABLE 2

Optional labels used for detection or responses by fluorescence microscopy as placed in a turret of a light microscope.
Filter Turret Positions

| Position | Label | Condition [Filter Parameters] | $\lambda$ex | $\lambda$em |
|---|---|---|---|---|
| 1 | DIC | Differential Interference Contrast | | |
| 2 | H33342 | ds DNA - H33342 [49 DAPI: G 365: FT 395: BP 445/50] | 488 | 550 |
| 3 | AlexaFlour 594 | [43 HE DsR: 550/25: FT 570: BP 605/70] | 590 | 617 |
| 4 | DAF-FM/PED6/ BODIPY | [38 HE GFP: BP 470/40: FT 495: BP 525/50] | 495 | 515 |
| 5 | MitoTracker Deep Red | [Cy5: HQ Cy5: C97420] | 644 | 665 |
| 6 | ER Tracker [21 HE Fur] | [Custom ER Tracker: C95760] | 374 | 430-640 |

Various cellular responses are optionally processed into a relative comparison of the magnitude of the response. Such a relative comparison may be graphically displayed and/or compared in a computer with a software program to detect differences in each parameter, convert them to a relevant comparative magnitude scale such as a 0-4 scale with 4 being the maximal response and 0 being no observable response, and optionally plotting the responses in a visually and easily recognizable format such as a flower plot. It is appreciated that detection and optionally identification of one or more EM does not require processing of the data and plotting in a flower plot. Detection and optionally identification of an EM can be done manually or computationally for each specific response measured and then compared by one of many other processes known in the art such as individual comparisons to controls. The use of cytospectrograms and optionally flower plots provides an improved method of rapidly detecting either automatically or by a user through visual recognition relative to the response spectrum of one or more positive controls.

One of skill in the art understands where all reagents and materials are commercially obtained. Illustratively, substrates such as glass slides, labels, and substrates are available from Sigma-Aldrich, Co., St. Louis, Mo. Methods involving conventional biological techniques are used in the process described herein and are well known to those of ordinary skill in the art. Such techniques are routinely found and described in detail in methodology treatises such as: Optical Fluorescence Microscopy From the Spectral to the Nano Dimension, Alberto Diaspro, Ed. Springer; 1st Edition. edition (Nov. 30, 2010) ISBN-10: 3642151744; Short Protocols in Cell Biology, Juan S. Bonifacino (Editor), Mary Dasso (Editor), Joe B. Harford (Editor), Jennifer Lippincott-Schwartz (Editor), Kenneth M. Yamada (Editor), Wiley (Feb. 10, 2004); Current Protocols in Cell Biology, Print ISSN: 1934-2500, particularly chapters 1, 2, 4, 8, and 18; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002; among others.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

Isolation of Sentinel Cells

Male and female adult oyster toadfish of body mass ranging from 100 gm through more than 900 gm are obtained from the Supply Department, Marine Resources Center, Marine Biological Laboratory and used following protocols reviewed and approved by the institutional animal care and use committees at Wayne State University (Detroit, Mich.) and the Marine Biological Laboratory (Woods Hole, Mass.). For isolation of Sentinel Cells (SC) the fish are captured from holding tanks supplied with running natural sea water using mesh fish nets using methods such that direct handling of the fish by investigators is minimized. The fish are then anesthetized by immersion in 25 mg/liter 3-aminobenzoic acid ethyl ester (MS-222; Sigma-Aldrich, Co., St. Louis, Mo.) in seawater in a Fish Carrier box. Anesthetized fish are identified by swimming belly-up and lack of response to pain stimuli.

Anesthetized fish are partially immobilized by intramuscular injection with 100 □l of 2.5 mg/ml pancuronium bromide (1,1'-[(2β,3α,5α,16β, 17β)-3,17-bis(Acetyloxy)androstane-2,16-diyl]bis(1-methylpiperidinium)dibromide) (Sigma-Aldrich Co., St. Louis, Mo.) in Artificial Perilymph (167 mM NaCl, 2.5 mM KCl, 1.5 mM $CaCl_2$, 1.0 mM $MgCl_2$, 50 mM Tris-Base, pH 7.2) to provide a dose of 50 μgkg or 25 μg for a 500 gm/fish. This allows easy placement in a stereotactic immobilization device. The fish are stereotactically secured in a fish immobilization box that is also filled with filtered seawater containing 25 mg/liter (25 μg/ml) MS-222 to maintain anesthesia.

To access the stationary macrophages of the vestibular labyrinths, the fish is placed into a custom-built Plexiglas sterotactic mounting box with sharpened stainless steel prongs. Prongs are advanced to impinge on established skeletal landmarks, i.e., lateral points on the skull, and the spine. A seawater moistened cloth is gently placed over the fish's eyes to prevent desiccation and preclude any potential (but never observed) related discomfort (i.e., during surgery and microscopic observations), obscure its vision, and to prevent desiccation of the eyes; this also serves to eliminate the visual cues that trigger a bite response.

The fish's cranium is opened using scalpels, curettes, and Mallelus nippers to expose the brain and neighboring vestibular labyrinths by making a 4-5 cm long rostral-caudal incision on the dorsal surface of the head—starting about 1 cm caudal of the caudal end of the eyes. The incision is then expanded to flaps with short lateral incisions from the first incision outward. The skin flaps are then retracted to expose the skull. Any "bleeder" vessels are dammed with small pieces of filter paper. The opened cranial space is filled with fluorocarbon FC-75 (3M Co., St. Paul, Minn.) or FC-70 (Sigma-Aldrich Co., St. Louis, Mo.) after collection of natural perilymph, which is stored at 4° C. for subsequent cell culture and manipulations. The labyrinths are located visually, and gently cut and teased away from surrounding mesentery tissue, blood vessels, and the $VIII^{th}$ nerve. The freed labyrinths are transferred to a culture dish containing 0.22 μm filter sterilized artificial perilymph. Following collection of labyrinths, the fish is euthanized by intramuscular (1M) injection of 600 μl of 100 mg/kg Ketamine.

The SC are isolated from the labyrinths by gently disassembling the labyrinths with venous scissors so as to cut them into cylinders about 1 mm in length followed by rotating the cylinders to rest with one cut-end against the surface of a culture vessel lined with a biocleaned glass coverslip of 0.17 mm thick. Culture vessels are filled with culture medium (L-15, Sigma-Aldrich, Co., St. Louis, Mo.) to a depth that insures that the canal cylinders are covered with about 1-2 mm of culture media.

Tissue laden culture vessels are transferred to an incubator, and maintained at room temperature in the absence of $CO_2$, antibiotics, antifungals, or serum. The SC migrate from the tissue to the glass coverslip. In some isolations the SC are collected following collagenase digestion of the labyrinth tissue followed by a 24 hour recovery time.

Example 2

Preparation of Biocleaned Glass Culture Substrate

The contents of a one ounce packet of 0.17 mm thick, 22 $mm^2$ glass coverslips are washed batch-wise as. Coverslips are added, one at a time, to a beaker containing 600 ml of 1% (v/v) Pierce RBS-pf detergent (Pierce Chemical Co., Rockford, Ill.) in tap water warmer than 45° C. Coverslips are soaked in this solution for 10 min, with gentle swirling for 10 sec each to assure that each coverslip is exposed to detergent solution. The detergent solution is decanted to waste. Coverslips are then resuspended in 600 ml of 1% (v/v) RBS-pf detergent in hot tap water, and subjected to sonication for 10 minutes, with mixing of the coverslips for 10-15 sec every minute. Coverslips are then rinsed 10 times with a gentle stream of hot tap water (temperature >45° C.). The coverslips and solution are gently swirled to assure adequate rinsing of all surfaces, and the tap water rinses are decanted to waste between each rinse. The coverslips are then rinsed 10 times with cold tap water, and the last wash is drained to waste. Coverslips are then transferred to 600 ml of distilled deionized water (e.g., 18 megOhm water) one at a time, using a pair of clean #5 forceps, and dipping in three separate beakers of "rinse" (i.e., 600 ml of distilled deionized 18 megOhm water). One edge of each coverslip is blotted against a piece of Whatman number 1 filter paper before placing into final beaker to minimize carry-over to the final water rinse. Coverslips are then suspended in 600 ml of distilled deionized 18 megOhm water and subjected to sonication for 10 min, with mixing of the coverslips for 10-15 sec every minute. Using a pair of clean #5 forceps, the coverslips are transferred to a final beaker of about 250 ml of 95% ethanol (EtOH) by dipping each coverslip through three rinses of 95% EtOH, and draining the coverslip against the beaker containing the wash ethanol before dipping in the next beaker of ethanol. One edge of each coverslip is blotted against a piece of Whatman #1 filter paper before placing into final beaker to minimize carry-over to this final EtOH rinse. Coverslips are swirled in this ethanol rinse as noted above for the water rinses. The rinse is decanted to waste, and the coverslips are resuspended in 95% EtOH. This step is repeated 6 times. The coverslips are then suspended in fresh 95% EtOH, and then subjected to a fifteen minute sonication. Coverslips are stored in a screw-top vessel in fresh 95% EtOH, or stored dry as follows.

For dry storage, a prepped coverslip is obtained by grasping a preprepped coverslip at a corner with a pair of #5 forceps, blotting one edge of each coverslip against a piece of Whatman #1 filter paper. The coverslip is dried with a four layer thick piece of lint free wipe being careful to avoid touching any surface with skin. The coverslip is polished with a four layer thick piece of lens paper. The clean, dry and polished coverslip is placed in an appropriate storage box, wrapped in plastic wrap or SARAN WRAP, and stored in a dry location.

Example 3

Labeling of SM for Detection of Energetic Materials (EM)

Single coverslips of cultured SC of Example 1 are labeled with fluorescent dyes to monitor responses.

For detection of DNA the intercalating dye DNA-specific bisbenzamide dye Hoechst H33342 (H21492; Molecular Probes, Carlsbad, Calif.) is used. Cells are labeled at a final concentration of 0.1 nM in media for 18-24 hours or 0.2 µg/ml in culture media for 20-30 minutes.

Phospholipase $A_2$ (PLA2) activity is monitored following labeling with N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6). A stock solution of PED6 is prepared by dissolving 1.0 mg PED6 with 1.0 ml of EtOH, i.e., 10 mg/ml PED6 in EtOH; dilute with 1.0 ml of 0.22 µm filtered artificial perilymph (167 mM NaCl, 2.5 mM KCl, 1.5 mM $CaCl_2$, 1.0 mM $MgCl_2$, 50 mM Tris-Base, pH 7.2] to a final concentration of 1.0 mg/ml. Stock solutions are stored in 50 µl aliquots at 10 mg/ml that are drop frozen in liquid $N_2$ and kept at −20° C. For labeling of SC, PED6 is added to culture media at a final concentration of 1 µg/ml.

For detection of nitric oxide synthase activity, cells are labeled with the fluorescent probe 4-amino-5-methylamino-2',7'-difluorofluorescein diacetate (DAF-FM diacetate; D-23844; $\lambda_{Ex}$: 495 nm; $\lambda_{Em}$: 515 nm; Molecular Probes/Invitrogen, Carlsbad, Calif.) at a final concentration of 1 µM in culture media for 10 minutes, or at 100 nM for up to 2 hours. DAF-FM-diacetate enters cells by facilitated diffusion, whereupon cytosolic esterases remove the acetate moieties leaving DAF-FM soluble and trapped in the aqueous cytosol. Nitric oxide produced in the labeled cytosol is then trapped by the DAF-FM which produces a fluorescent triazole at intracellular pHs that is about 160-fold more intense than the un-reacted DAF-FM diamine, and which is readily monitored with a light microscope.

Mitochondria in SC are labeled with MitoTracker Deep Red (M22426, Invitrogen, Inc., Carlsbad, Calif.). Stock solutions of MitoTracker Deep Red FM are prepared at a concentration of 100 nM in DMSO. Sentinel Cells are labeled at a concentration of 0.1 nM MitoTracker Deep Red FM in L-15 culture media, for periods of 1-4 hours. Solutions are used on the day they are prepared, and are maintained in ice until needed.

Labeling of the ER is accomplished by incubating SC cells with 100 nM-1 uM fluorophore conjugated glibenclamide (ER-TRACKER, Invitrogen Corp., Carlsbad, Calif.) in L-15 media or HBSS at ambient temperature or 37° C. for 15-30 minutes.

Each of the fluorescent labels are incubated with SC simultaneously in L-15 media at the above concentration. The media is exchanged for fresh media and the SC are used in subsequent determinations of the presence or absence of EM.

Example 4

Exposure of Sentinel Cells to RDX

Sentinel Cells prepared as in Example 1 and labeled as in Example 3 are exposed to RDX 50 nm in solution. The entire exposure time is monitored by light microscopy and scanning electron microscopy (by standard techniques). Light microscopy is performed with a Zeiss AxioObserver D1M microscope (Carl Zeiss, Thornwood, N.Y.) equipped with a 1.4 NA condenser, optics for differential interference contrast (DIC) using linear polarized light with an LED illuminator, and episcopic illumination with an X-Cite® Series 120 illuminator and liquid light guide (Scientifica, East Sussex, UK) and appropriate filter cubes for fluorescence, a Zeiss AxioCam HSm monochrome digital camera and high-speed image acquisition hardware and software. The microscope operated using Zeiss AxioVision software to control the instrument, image acquisition, and processing and analysis of the images obtained.

Cells are observed with a Zeiss 40×, 1.1 NA LD C-apochromat water immersion objective lens (Zeiss 44 44 57) with 40×, 1.2 W III DIC prism slider. Data are recorded in "real-time" onto RAID 1 hard disk arrays (Maxtor OneTouch™ III Turbo Edition, Maxtor, Scotts Valley, Calif.). The microscope is mounted onto either a TMC Model 61 or a TMC Model 63 vibration isolation table (Technical Manufacturing Company, Peabody, Mass.) operated at a suspension pressure of 75 psi of dry $N_2$ gas. Cells and tissues are observed on biocleaned coverslips prepared as in Example 2 mounted onto a custom-designed and manufactured coverslip holder that facilitates observations, perfusions, and long-term culturing. The Zeiss C-Apochromat 40×, 1.15 NA DIC III water immersion objective lens is used for both differential interference contrast and fluorescence microscopy.

For monitoring of chromosomal DNA responses and nucleus responses, the mean fluorescence emission intensity of twenty H33342-labeled (diploid) erythrocyte nuclei are viewed with a Zeiss fluorescence filter set 49 filter cube, which are considered to represent 5.6 pg of DNA. (Hinegardner, R. and Rosen, D. L., *Amer. Natural.*, 1972; 106:621-644.) Extracellular background (which is observed to remain constant and consistent with unlabeled control cultures) is considered to represent 0 pg of DNA. Emission intensities are within the linear range of the AxioCam HSm camera that is operated at a bit-depth of 12 bits using the AxioCam controller module within AxioVision software. The fluorescence emission intensity of H33342—labeled sentinel cell nuclei are recorded and measured, the distribution and relative levels of heterochromatin and euchromatin measured, and their content compared to the mean value for diploid erythrocyte nuclei; data are expressed in either pg DNA per nucleus or as fluorescence emission intensity relative to diploid erythrocytes. Fluorescence emission intensities as sums of pixel intensities are determined from entire nuclei outlined in AxioVision and values entered into and analyzed with AxioVision, Excel and SigmaStat routines.

For detection of NO, a Zeiss filter cube 38 HE GFP is used. Fluorescence emission intensities as sums of pixel intensities are determined from entire cells outlined in AxioVision and values entered into and analyzed with AxioVision, Excel and SigmaStat routines. Extracellular background (which are observed to remain constant and consistent with unlabeled control cultures) is considered to represent null levels of NO and NOS activity. These labeling methods are consistent with methods to quantitate endogenous and inducible NOS activity in subsequent studies. (Strijdom, H., et al., *J. Mol. Cell. Cardiol.*, 2004; 37:897-902.)

SC contrast is provided by differential interference contrast microscopy (DIC) in position 1 of the device filter turret. This provides for cell localization as well as visualization of SC morphological responses.

Mitochondria responses are monitored by alterations in Mitotracker Deep Red staining.

Responses in the endoplasmic reticulum are viewed by monitoring ER-Tracker staining.

Each of the differentially observed fluorescent markers are observed in real time with any underlying response in the SC. The microscope is outfitted with a proper filter set in relative turret positions as depicted in Table 1.

Figure 2A:
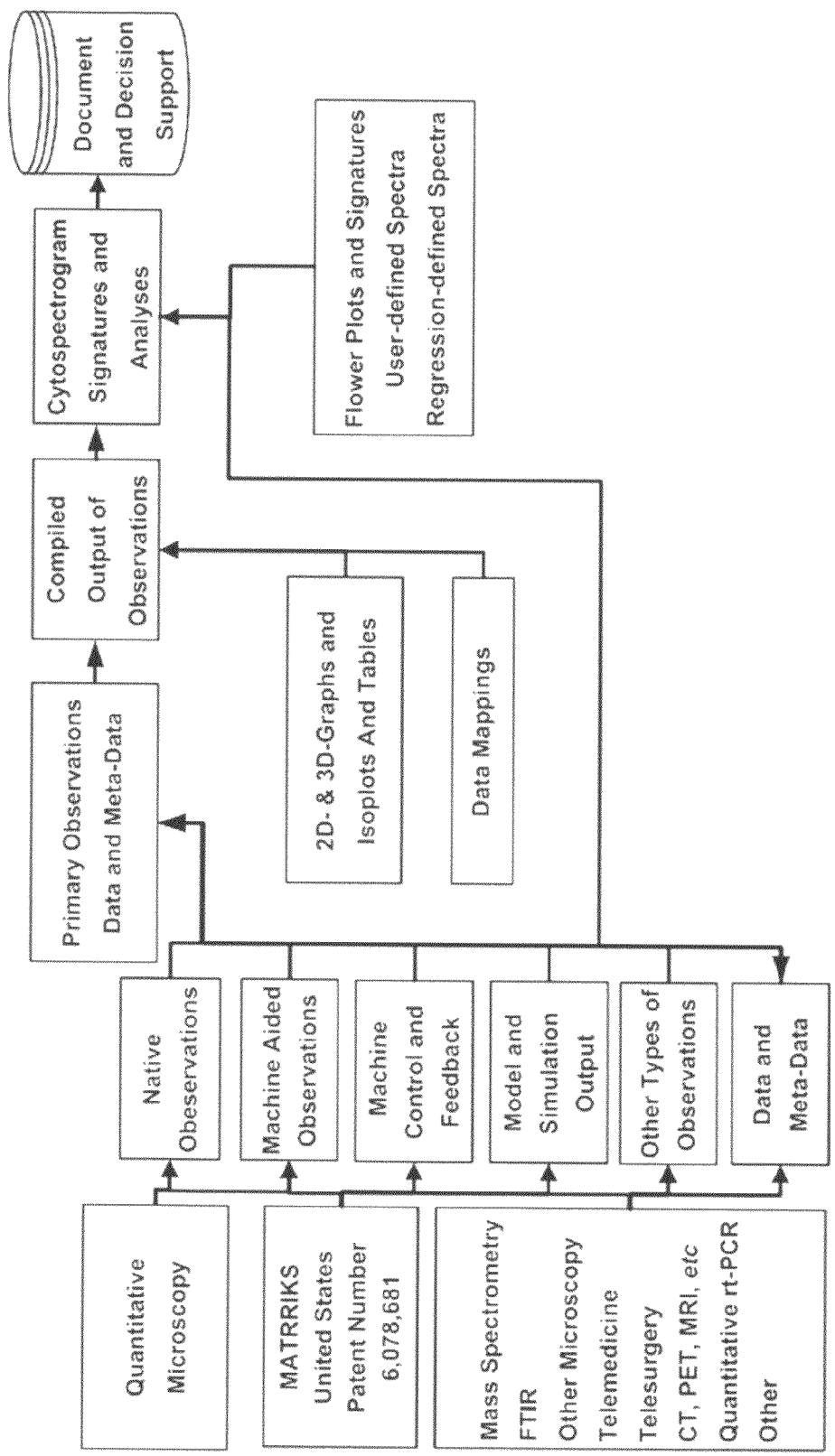
FIGS. 2A and B are flow charts of methods used to relatively quantify and interrelate observations in changes in sentinel cells upon exposure to a control or energetic material as well as construction of cytospectrograms and flower plots for ready visual identification of an EM exposed to the sentinel cells.
Figure 2B:
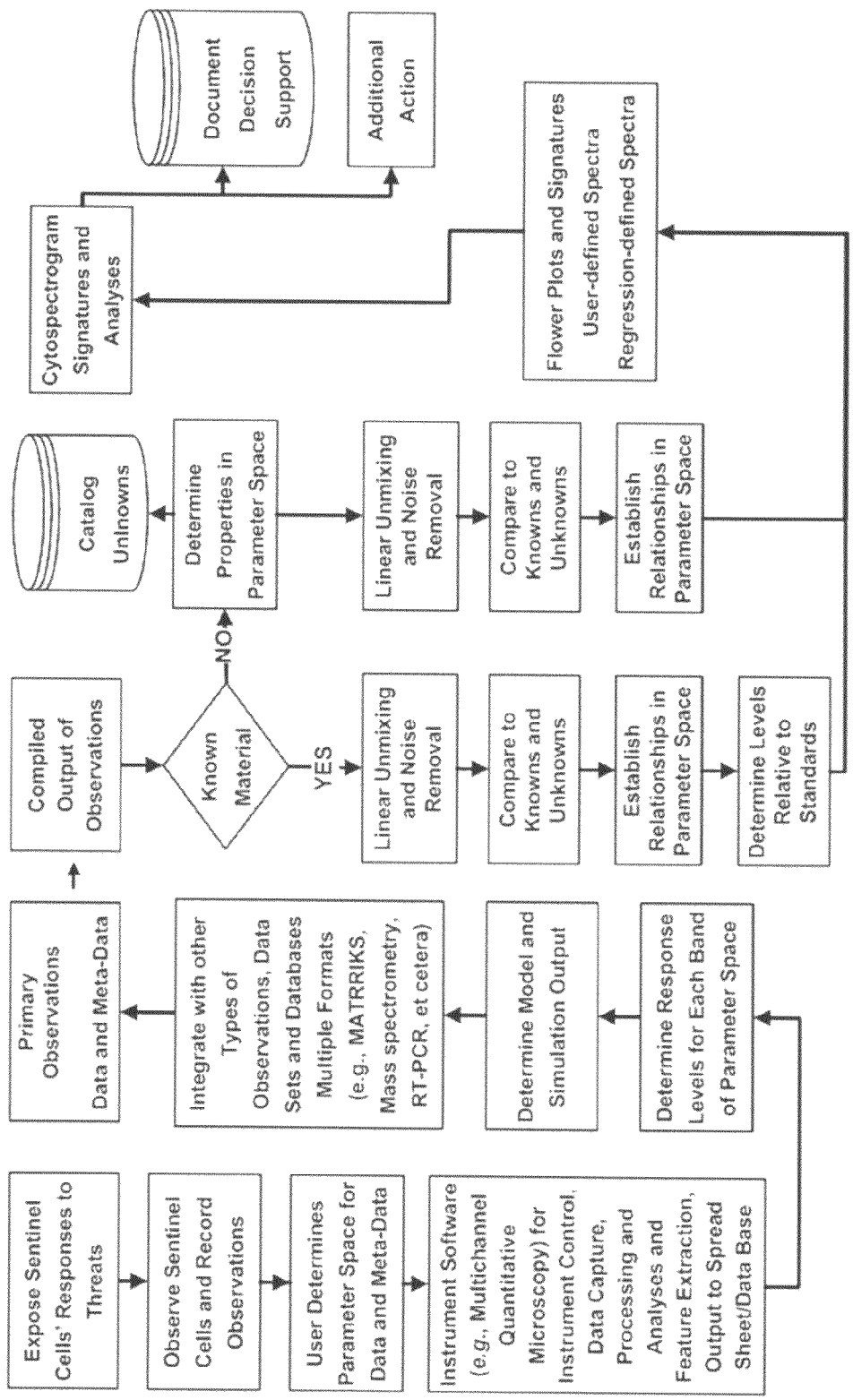
FIG. 2C is a relative and quantitative illustration of cellular responses to various EM and comparisons to controls.
FIG. 2D is an illustrative microscopic image depicting sentinel cells prior to an following exposure to RDX.
FIG. 2E is an illustrative flower plot of various cellular responses interrelated and graphically displayed in an EM specific pattern in one embodiment using RDX as an EM where the responses are as in Table 1.

Data are collected and processed as depicted in FIGS. 2A and 2B.

Figure 2C:
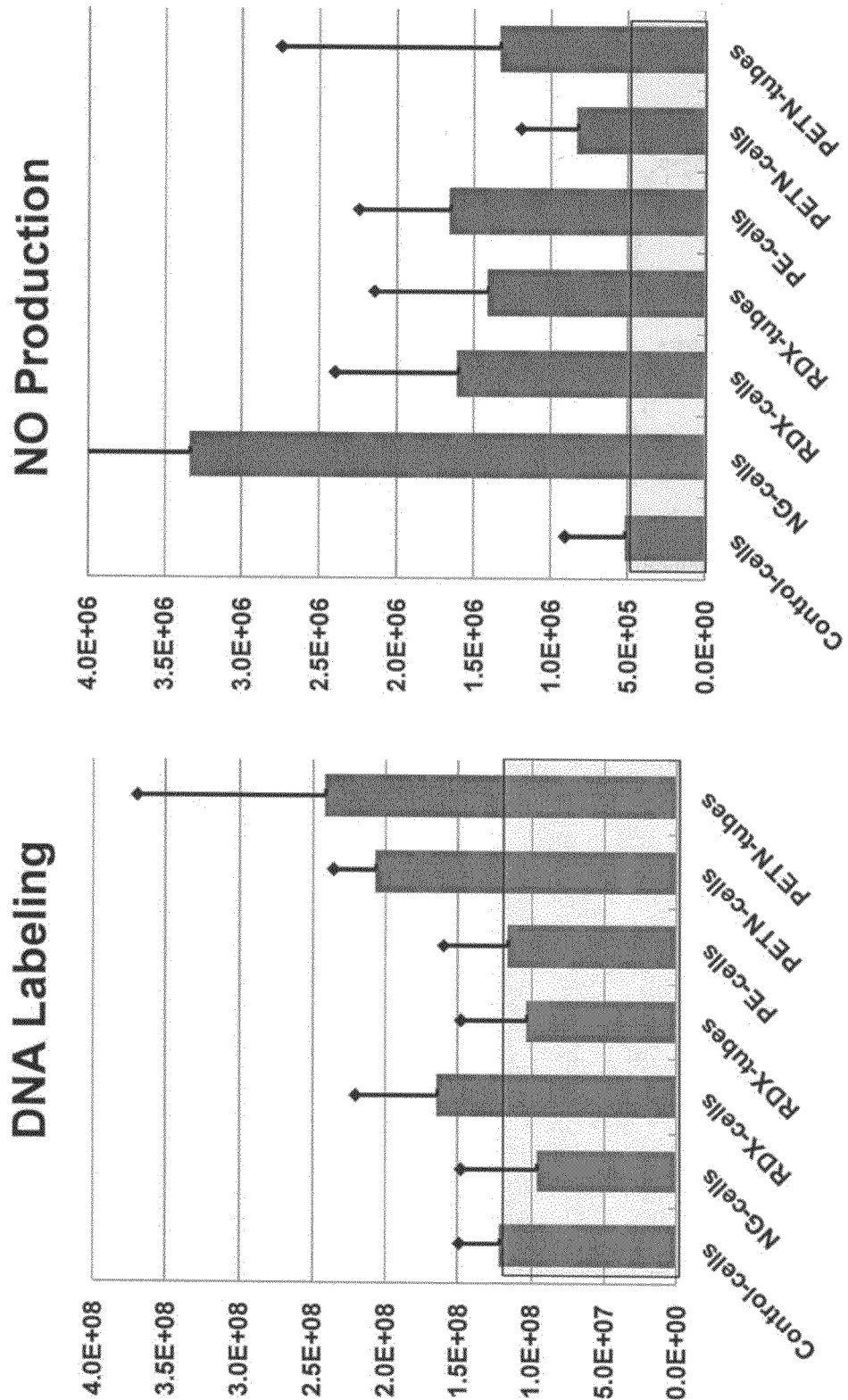
Figure 2D:
Figure 2D:
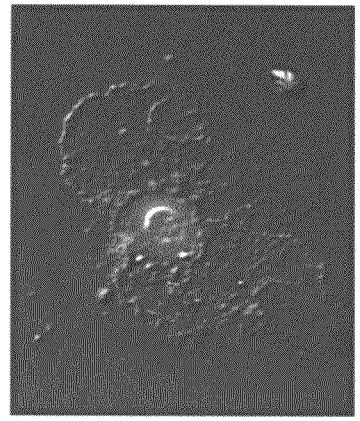
Figure 2E:
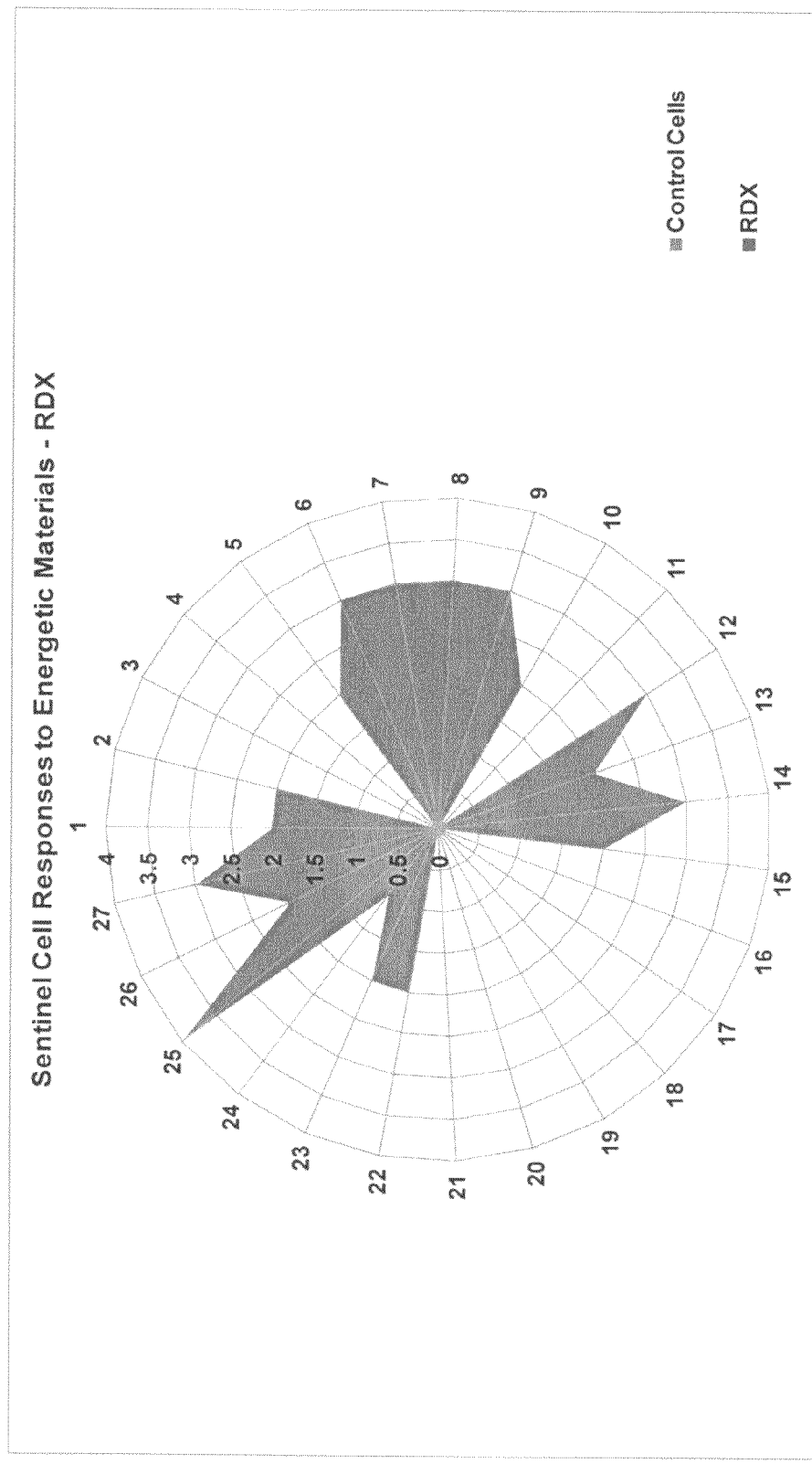

FIG. 2C illustrates labeled DNA fluorescence and nitric oxide level changes following exposure of isolated sentinel cells to various energetic materials in a quantitative comparison demonstrating statically significant increases over control for several energetic materials. These data are combined with other data obtained by fluorescent microscopy to identify an EM following exposure of sentinel cells to the EM. As illustrated in FIG. 2D, exposure to RDX, as one example, results in a marked increase in cytoplasmic NO levels within 10 minutes of exposure. Also observed are chromosome condensation; unscheduled dsDNA synthesis; increased nuclear dsDNA; arborized nuclei; large changes in cell morphology; distended mitochondria; loss of nuclear dsDNA; and leakage of dsDNA to cytosol and extracellular space. FIG. 2E illustrates the relative changes in SC response over a full spectrum of analyzed responses. This pattern is unique to RDX.

As a set of controls, SC are independently exposed to pentaerythritol (PE), glycerol, or dimethyl sulfoxide. No responses are observed with any of the control agents.

Example 5

Exposure of Sentinel Cells to PETN

Figure 3A:
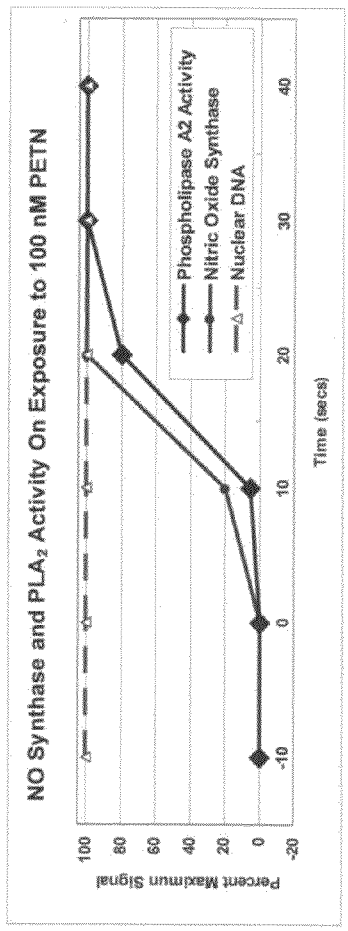
Figure 3B:
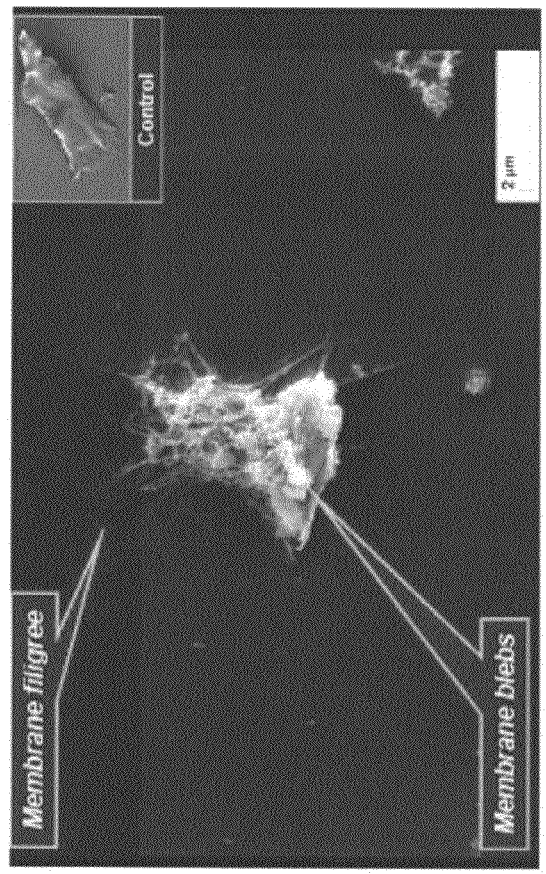
Figure 3C:
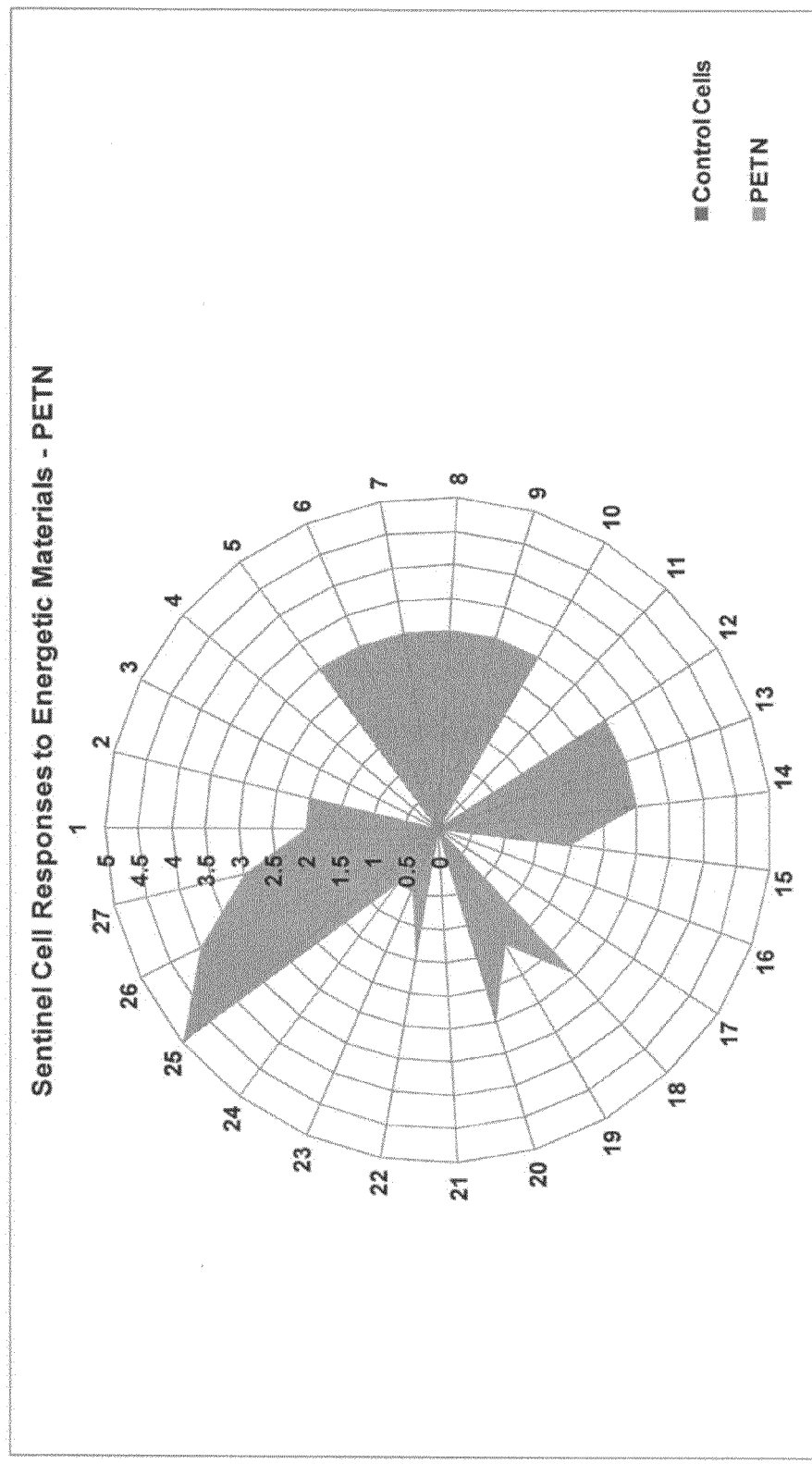

Sentinel Cells prepared as in Example 1 and labeled as in Example 3 are exposed to PETN at 50 nm in solution. The entire exposure time is monitored by light microscopy as in Example 4. A nearly immediate NOS response is observed (within 20 seconds). (FIG. 3A). Also as depicted in FIG. 3A, a rapid increase in phospholipase A2 activity is observed. Changes in membrane structure upon exposure to PETN are illustrated in FIG. 3B compared to control (inset). Marked changes in structure including present of significant membrane filigree and membrane blebs are observed. As shown in the flower plot of FIG. 3C, SC cells exposed to PETN show increase in cytoplasmic NO levels, marked increases in nuclear dsDNA, induction of chromosome condensation, unscheduled DNA synthesis, induction of filigree deformations, fragility in cell membranes, and cell pairs observed at a low percentage. The relative levels of and identity of these changes in sentinel cells is specific to exposure to PETN.

Example 6

Exposure of Sentinel Cells to HMX

Sentinel Cells prepared as in Example 1 and labeled as in Example 3 are exposed to HMX at 0.5 nm in solution. The entire exposure time is monitored by light microscopy as in Example 4.

The observed response types, but not the magnitudes, are similar to that observed for RDX but at 100-fold lower levels of EM. The primary responses observed included loss of nuclear dsDNA to cytoplasmic space, then to extracellular space; increase in extra-nuclear dsDNA; arborized nuclei and cell morphologies; ell pairs observed (low percentage). The responses are plotted in a flower plot as in FIG. 4A with a phase contract image depicted in FIG. 4B. The relative levels of and identity of these changes in sentinel cells is specific to exposure to HMX.

Example 7

Exposure of Sentinel Cells to TNT

Sentinel Cells prepared as in Example 1 and labeled as in Example 3 are exposed to TNT at 50 nm in solution. The entire exposure time is monitored by light microscopy as in Example 4.

Figure 5A:
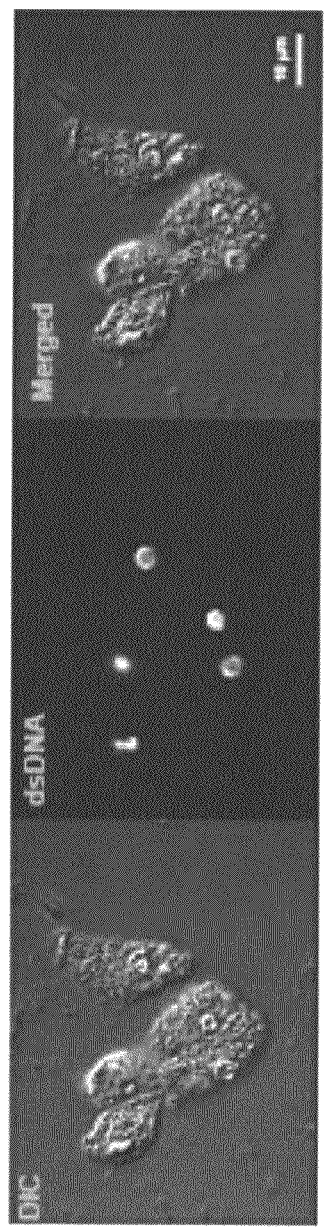
Figure 5B:
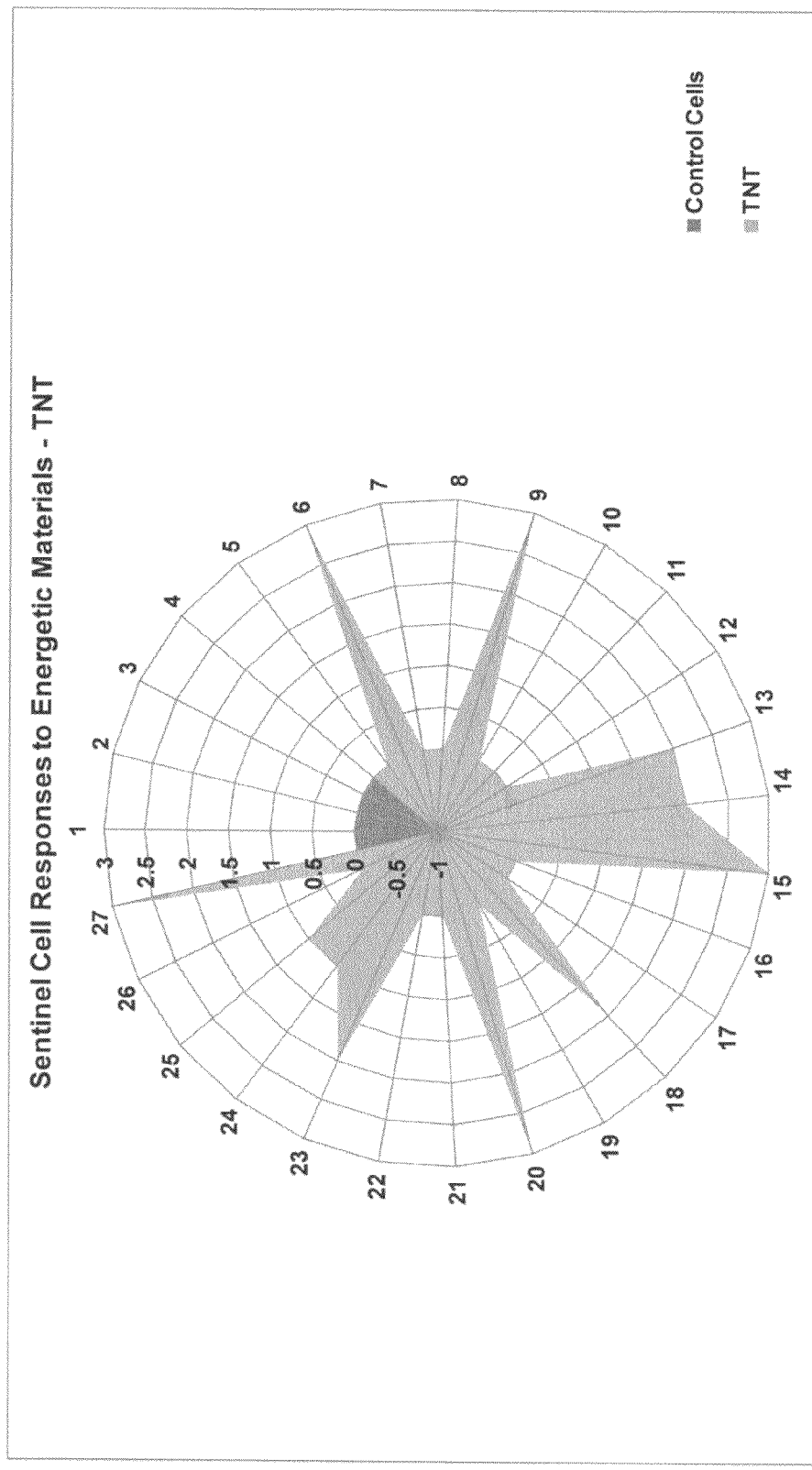

Specific responses include micronuclei and apoptotic nuclear dsDNA arrangement/loss; effect is more pronounced in unfertilized eggs; observed effects include mechanisms integral to odor detection in canine olfactory cells. FIG. 5A illustrates morphological changes in sentinel cells upon exposure to TNT. The identity and relative magnitude of all tested responses are plotted in a flower plot as in FIG. 5B and are specific for TNT.

Example 8

Exposure of Sentinel Cells to Volatiles from C4

Sentinel Cells prepared as in Example 1 and labeled as in Example 3 are exposed to 1 gram of C4 placed within 6 cm of the cells (under 1 mm depth of media) such that aerosols contact the media surface and thereby diffuse to contact the SC. The entire exposure time is monitored by light microscopy as in Example 4.

As is illustrated in FIGS. 6A, B, and C observed responses include: a loss of nuclear dsDNA to cytoplasmic volume then to extracellular space; a marked increase in extra-nuclear dsDNA; formation of micronuclei; arborized nuclei and cell morphologies; plasma membrane blebbing and perforations (porocytotic); and cell pairs are observed (low percentage). The identity and magnitude of all tested responses are plotted in a flower plot as in FIG. 6C and are specific for volatiles from C4.

Example 9

Exposure of Sentinel Cells to Volatiles from Commercial Preparation of Semtex A1

Sentinel Cells prepared as in Example 1 and labeled as in Example 3 are exposed to 1 gram of Semtex A1 (commercial) placed within 6 cm of the cells (under 1 mm depth of media) such that aerosols contact the media surface and thereby diffuse to contact the SC. The entire exposure time is monitored by light microscopy as in Example 4.

Figure 7A:
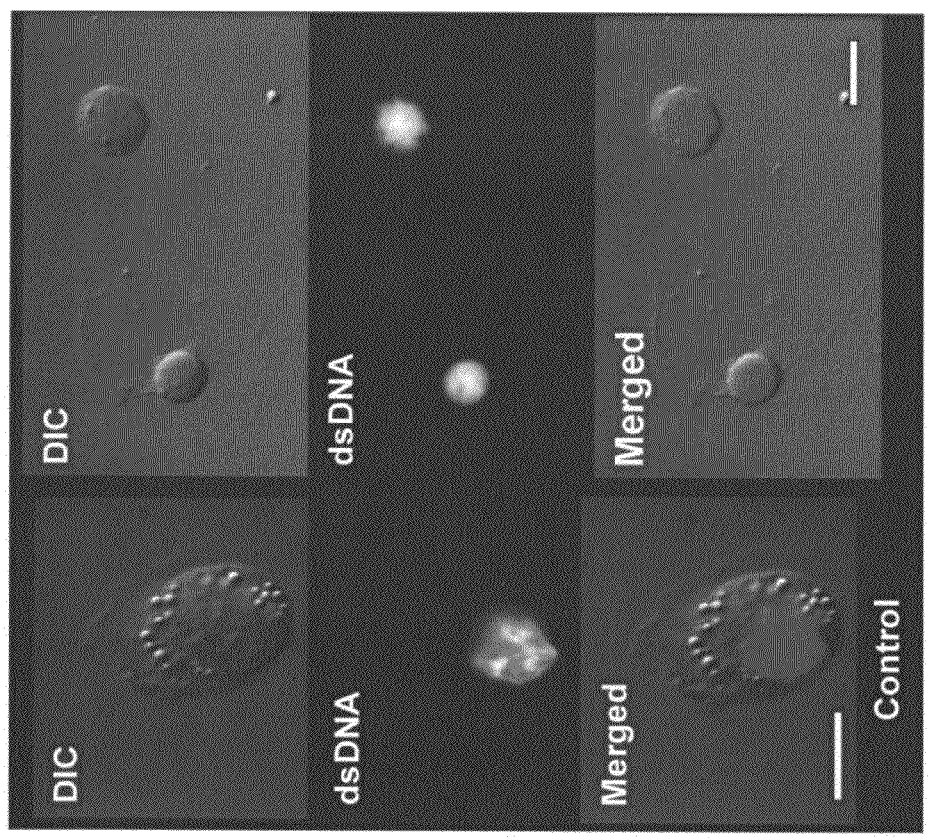
Figure 7B:
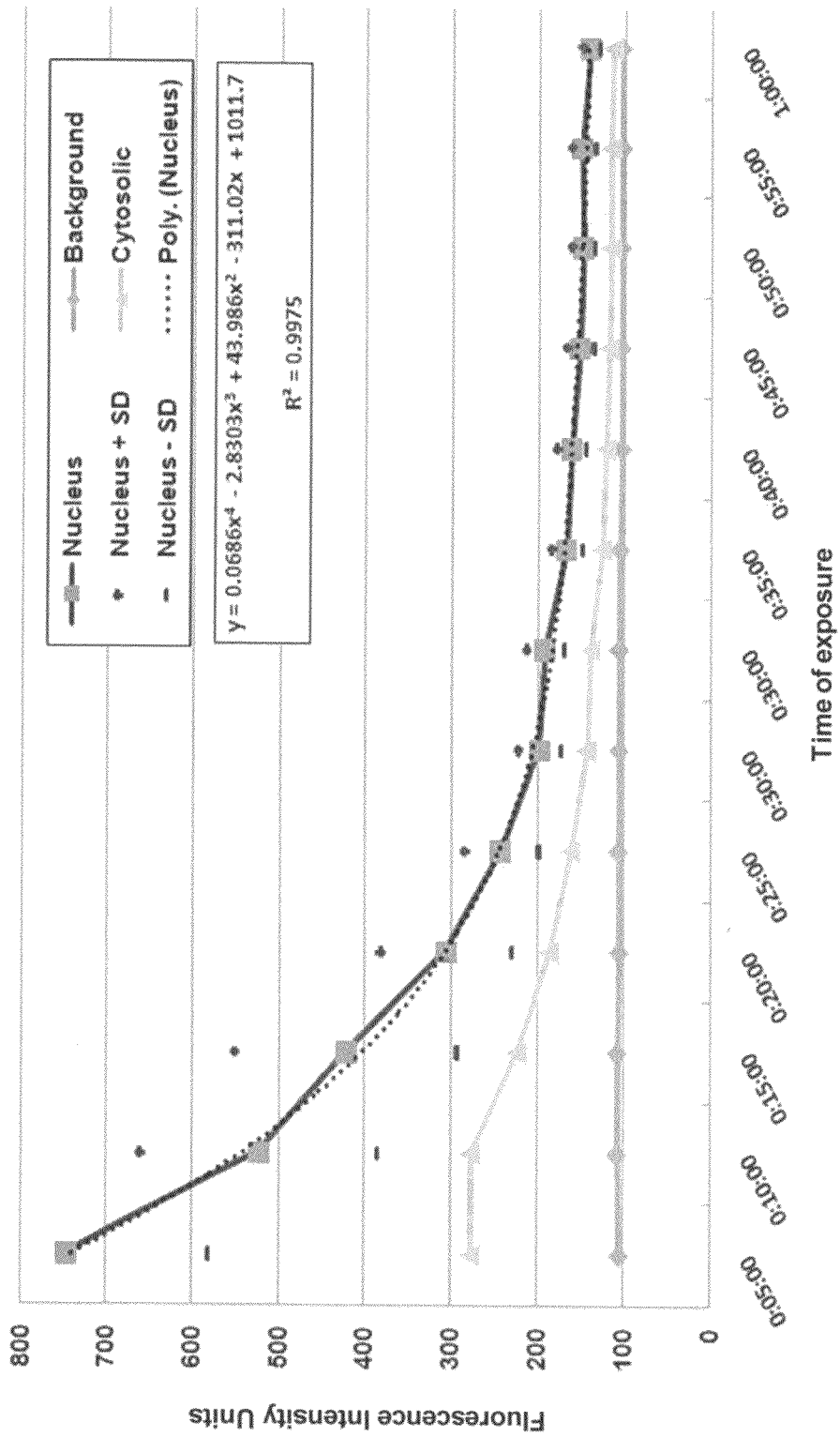
Figure 7C:
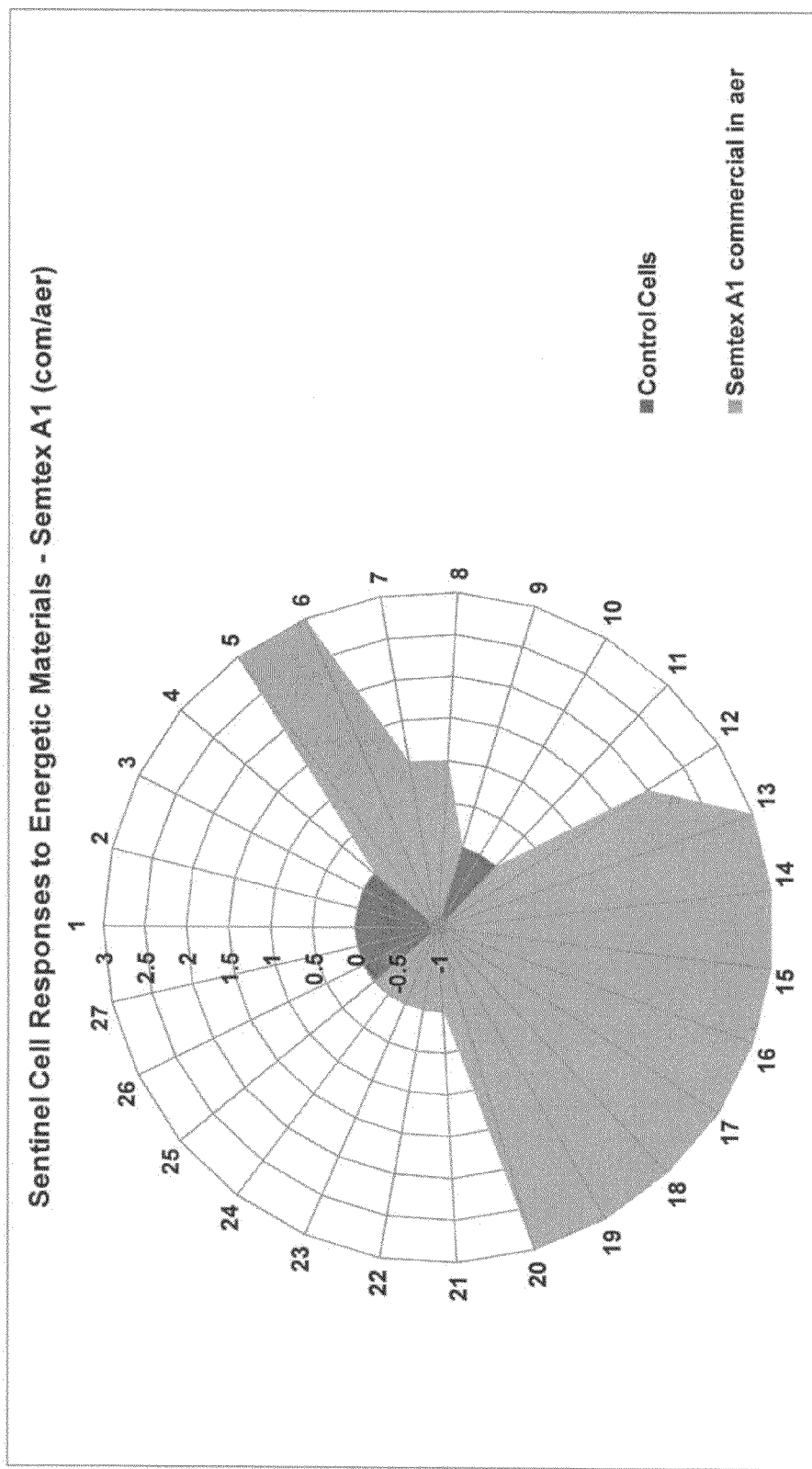

As is illustrated in FIGS. 7A-C, observed responses include: loss of nuclear dsDNA to cytoplasmic volume then to extracellular space; a marked increase in extra-nuclear dsDNA; chromatin clumping; arborized nuclei and cell morphologies; plasma membrane blebbing and perforations cell pairs observed (low percentage). The identity and magnitude of all tested responses are plotted in a flower plot as in FIG. 7C and are specific for volatiles from Semtex A1.

Example 10

Exposure of Sentinel Cells to Lipopolysaccharide (LPS) from *Escherichia coli* Serotype 055

Sentinel Cells are prepared as in Example 1 and labeled as in Example 3. The cells are exposed to LPS-Alexa Fluor 594 conjugate. The entire exposure time is monitored by light microscopy as in Example 4. Lipopolysaccharide (LPS) is a known component for *E. coli* and is used as a stimulant to elicit activation of and opsinization responses in macrophages. Internalization by SC is observed as fluorescent endosomes.

Briefly, stock solutions of LPS from *Escherichia coli* serotype 055:B5 conjugated with Alexa Fluor 594 conjugate (Invitrogen, Corp., Carlsbad, Calif.) are prepared at 10 µg/ml with 0.2 µm filter sterilized artificial perilymph. Stock solutions are stored in 10 µl aliquots at 10 µg/ml that are drop frozen in liquid $N_2$ and kept at −80° C. Assays are performed using LPS from *Escherichia coli* serotype 055:B5 conjugated with Alexa Fluor 594 conjugate diluted to 200 µg/ml stock 50 µl to 1 ml L-15 for 1.0 µg/ml.

LPS responses are observed in SC. As LPS forms micelles, 0.001% glycerol which is found to not elicit a Sentinel Cell response.

Example 11

Exposure of Sentinel Cells to Mycoplasma

Sentinel Cells are prepared as in Example 1 and labeled as in Example 3. Sentinel Cells will aggressively attack mycoplasma and remove them from a culture. This can be observed and quantified with a light microscope using differential interference contrast optics, and fluorescence for dsDNA as described above.

Cells are exposed to mycoplasma using the Invitrogen Vybrant Phagocytosis Assay Kit (Prod. No. V-6694, Invitrogen Corp. Carlsbad, Calif.). Briefly, SC are cultured for 2 days before performing the response assay. Exposure to mycoplasma produces a distinguishable set of responses.

Example 12

Exposure of Sentinel Cells to TNG

Sentinel Cells prepared as in Example 1 and labeled as in Example 3 are exposed to TNG at 0.5 nm in solution. The entire exposure time is monitored by light microscopy as in Example 4.

Primary responses observed included pronounced NOS activity, significant increases in cell size and membrane surface, pronounced hunting behavior, and levels of apoptosis. The responses are plotted in a flower plot as in FIG. 8 and are specific to TNG.

Example 13

Exposure of Sentinel Cells to DMDNB

Sentinel Cells prepared as in Example 1 and labeled as in Example 3 are exposed to DMDNB at 5 nm in solution (88 ppt). The entire exposure time is monitored by light microscopy as in Example 4.

Figure 9A:
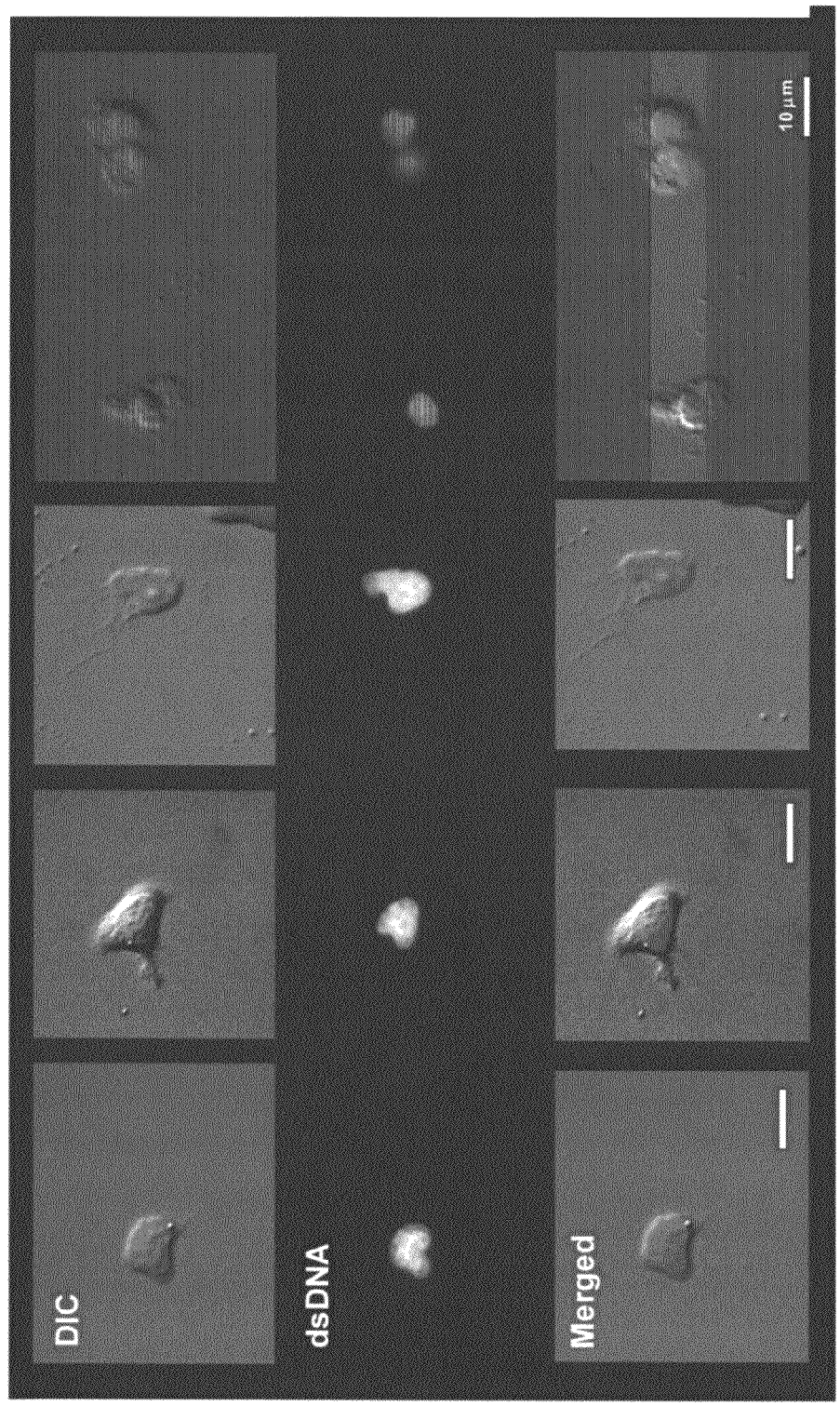
Figure 9B:
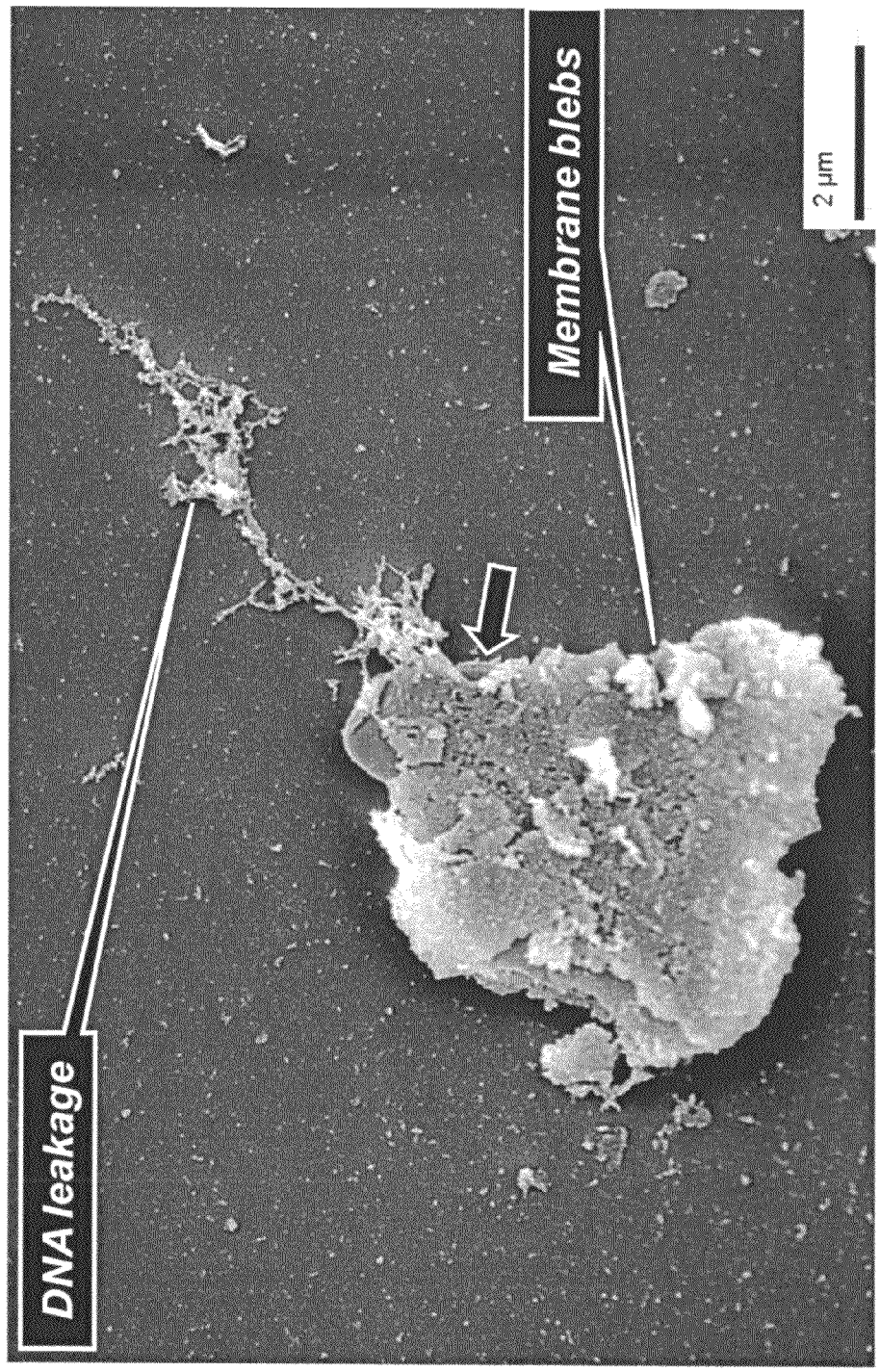
Figure 9C:
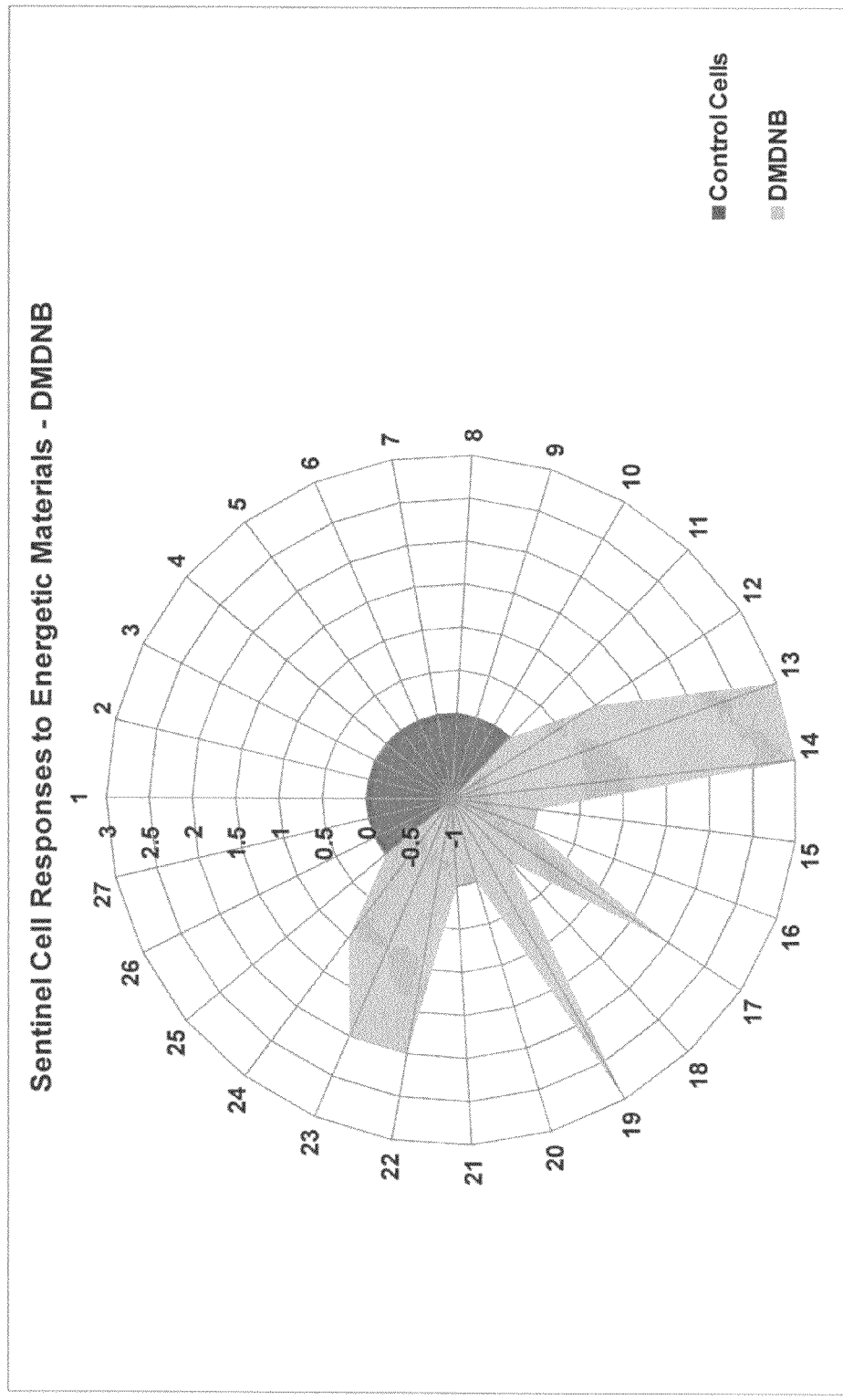

As is illustrated in FIGS. 9A-C Primary responses observed included pronounced lobed nucleus and nucleus with tines, arborized nucleus, highly condensed chromosomes, and significantly increased nuclear envelope breakdown, mitosis, and emerge from tissue. The responses are plotted in a flower plot as in FIG. 9C and demonstrate a pattern specific to exposure to DMDNB.

Example 14

Exposure of Sentinel Cells to *Escherichia coli* K12

Sentinel Cells are prepared as in Example 1 and labeled as in Example 3. The entire exposure time is monitored by light microscopy as in Example 4.

Cells are exposed to *E. coli* K12 using the Invitrogen Vybrant Phagocytosis Assay Kit (Prod. No. V-6694, Invitrogen Corp. Carlsbad, Calif.). Briefly, SC are cultured for 2 days before performing the response assay. Exposure to *E. coli* K12 results in phagocytosis of the *E. coli* without the effects on nuclear dsDNA as is observed with many EM. FIG. 10.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof.

The invention claimed is:

1. A system for the detection of an energetic material comprising:
    an isolated stationary macrophage cell isolated from a vestibular labyrinth of a *Opsanus* sp.;
    said cell contacting a substrate selected from the group consisting of glass;

said cell contacting one or more energetic materials selected from the group consisting of 1,3,5-trinitro-1,3,5-triazacyclohexane, 2,2-bis(hydroxymethyl)1,3-propanediol, 1,3,5,7-tetranitro-1,3,5,7-tetrazocane, 2,4,6-trinitrotoluene, C4, Semtex Al, 1,2,3-trinitroxypropane, and 2,3-dimethyl-2,3,-dinitrobutane;

said cell exhibiting a set of cellular responses characteristic of and specific to said energetic material, said cellular responses selected from the group consisting of NOS activity, plateau of NO levels, sustainment of NO levels, increases or decreases in double stranded DNA, increases in nuclear DNA levels, unscheduled DNA synthesis, increase in cell size (diameter on surface), increased membrane surface, membrane blebbing, membrane peroxidation, increased cytoskeleton, enlarged nucleus, lobed nucleus, nucleus with tines, nuclear swell-relax, cytoplasmic DNA, aborization of the nucleus, formation of micronuclei, chromosome condensation, karyomeres, mirror image cells, breakdown of the nuclear envelope, onset of mitosis, emergence from tissue, hunting behavior, induction of apoptosis, and combinations thereof.

2. The isolated cell of claim 1 wherein said cell is immersed in media.

* * * * *